United States Patent
Intes et al.

(10) Patent No.: US 8,565,862 B2
(45) Date of Patent: Oct. 22, 2013

(54) OPTICAL IMAGING METHOD FOR TISSUE CHARACTERIZATION

(75) Inventors: Xavier Intes, Montréal (CA); Salim Djeziri, Montréal (CA)

(73) Assignee: Softscan Healthcare Group Ltd., Tortola (VG)

( * ) Notice: Subject to any disclaimer, the term of this patent is extended or adjusted under 35 U.S.C. 154(b) by 1195 days.

(21) Appl. No.: 11/575,972

(22) PCT Filed: Sep. 26, 2005

(86) PCT No.: PCT/IB2005/002846
§ 371 (c)(1),
(2), (4) Date: Jul. 9, 2008

(87) PCT Pub. No.: WO2006/032997
PCT Pub. Date: Mar. 30, 2006

(65) Prior Publication Data
US 2009/0005692 A1    Jan. 1, 2009

Related U.S. Application Data

(60) Provisional application No. 60/612,519, filed on Sep. 24, 2004.

(51) Int. Cl.
    *A61B 6/00* (2006.01)
(52) U.S. Cl.
    USPC ............................ 600/477; 600/475; 600/407
(58) Field of Classification Search
    USPC ........................................ 600/477, 407, 475
    See application file for complete search history.

(56) References Cited

U.S. PATENT DOCUMENTS

| | | | |
|---|---|---|---|
| 5,345,941 A | 9/1994 | Rava et al. | |
| 5,899,865 A | 5/1999 | Chance et al. | |
| 6,665,556 B1 | 12/2003 | Alfano et al. | |
| 2002/0033454 A1* | 3/2002 | Cheng et al. | 250/339.12 |
| 2004/0215072 A1* | 10/2004 | Zhu | 600/407 |

FOREIGN PATENT DOCUMENTS

WO    WO99/65394    12/1999

OTHER PUBLICATIONS

American Cancer Society, Cancer Facts and Figures 2004, Atlanta, GA, 2004, pp. 1-60.
Cutler, Surg, Gynecol. Obstret., Jun. 1929, vol. 48, pp. 721-729.
Gros et al., J. Radiol. Electrol. 1972, vol. 53, pp. 297-306.
Alveryd et al., Cancer, Apr. 15, 1990, vol. 65, pp. 1671-1677.
Kincade, Laser Focus World, Jan. 2004, pp. 130-134.
Yodh et al., Physics Today, Mar. 1995, vol. 48, pp. 34-40.
Intes, Xavier et al., Radiologic Clinics of North America 43, Jan. 2005, pp. 221-234.

\* cited by examiner

*Primary Examiner* — Tse Chen
*Assistant Examiner* — Joel F Brutus
(74) *Attorney, Agent, or Firm* — McCarter & English, LLP

(57) ABSTRACT

There is provided a method for detecting and characterizing abnormalities within biological tissues. The method involves the characterization of the optical properties of the tissue to derive relative values of physiological properties between normal and suspicious regions of the tissue. In some aspects of the invention optical imaging and other imaging modalities are combined to detect and identify a disease state of the tissue.

30 Claims, 30 Drawing Sheets

OPTICAL IMAGING METHOD FOR TISSUE CHARACTERIZATION

CROSS-REFERENCE TO RELATED APPLICATION

This application claims priority from U.S. provisional application No. 60/612,519 entitled "OPTICAL IMAGING METHOD FOR TISSUE CHARACTERIZATION" filed on Sep. 24, 2004.

TECHNICAL FIELD

This invention relates to the field of optical characterization and molecular imaging of biological tissues. More specifically the invention relates to the detection of and imaging of abnormalities in tissues by optical methods.

BACKGROUND OF THE INVENTION

Optical techniques based on the Near-infrared spectral window have made significant progress in biomedical research in recent years. The relative low absorption and low scattering in the 600-1000 nm spectral range allow detection of photons that have traveled through several centimeters of biological tissue. Coupled with accurate models of light propagation, NIR techniques enable imaging of deep tissue with boundary measurements using non-ionizing, low dose radiation.

The interest in NIR techniques is fueled by the ability of the techniques to monitor functional tissue parameter such as oxy- and deoxy-hemoglobin and the development of appropriate low cost instrumentation. Based on these qualities, NIR optical imaging is expected to play a key role in breast cancer detection, characterization and monitoring through therapy; brain functional imaging and stroke monitoring; muscle physiological and peripheral vascular disease imaging. For all these applications, NIR techniques rely on endogenous contrast such as tissue hemodynamics.

One particular example of a potential application of optical imaging is breast cancer. Breast cancer is a major health problem worldwide. In North America, it is estimated that in the United States approximately 266,471 (American Cancer Society. *Cancer Facts and Figures* 2004. Atlanta, Ga., 2004) and in Canada 21,200 (Canadian Breast Cancer Foundation, *Breast Cancer Facts*, Toronto, ON, 2004) new cases of breast cancer will be diagnosed among women in 2004. Furthermore, 40,110 women in the U.S and 5,200 women in Canada will die from it. Incidence rates have begun to stabilize over the last ten years but continue to increase. It is estimated that one in eight American women and one in nine Canadian women will develop breast cancer at some point during their lifetime. But thanks to earlier detection and more effective treatments, the mortality rate for women of all races combined declined by 2.3% annually between 1990 and 2000.

Optical techniques for imaging the breast can be tracked back to the late 20's with the work of Ewings (Ewing, 3rd edition. Philadelphia, Saunders, Philadelphia, 1928) and Cutler (Cutler. Surg. Gynecol. Obstret. (1929); 48:721-9) who presented the first clinical results using optical techniques. Since then the technology has evolved, leading to enhanced systems in the 70's (Gros et al. J Radiol Electrol Med Nucl, (1978); 53:297-306) and commercial products in the 80's (Carlson. Spectrascan, S. Windosr, Conn., 1982) (10 Litescan, Spectrascan) that ultimately failed to receive acceptance as clinical modalities due to inconclusive results (Alveryd et al. Cancer (1990); 65:1671-1677).

Despite this setback, optical techniques have received steady attention in the last decade (Kincade. Laser Focus World January 2004; 130-4). The main reasons for this surge in interest reside in the development of new mathematical models able to describe accurately and quantitatively the propagation of light in biological tissues (Yodh et al. Physics Today (1995); 48:34-40). These mathematical models applied to multi-spectral measurements, are the foundation of diffuse optical spectroscopy (DOS) and diffuse optical tomography (DOT) (X Intes et al. Radiologic Clinics Of North America, January 2005).

Alternative methods for breast cancer detection such as X-ray mammography are widely used but do not always provide enough information to enable a conclusive diagnosis to be made. Thus other, complementary tests must be used, such as biopsy or blood tests, which can be invasive and may require a long time to complete.

There is therefore a need for methods to better detect spatial variations of chromophores in biological tissue, and to image spatial distributions thereof.

SUMMARY OF THE INVENTION

The present invention provides a method that overcomes the deficiencies of the prior art by providing a method and an apparatus for detecting an abnormality within a tissue by obtaining optical data from at least two positions within the tissue and for the pair-wise comparison of the values to generate a ratio thereof, which ratio is indicative of the presence of the abnormality.

In one embodiment of the invention the optical information is used to obtain a physiological property of the tissue which, in turn, can serve as the basis for the ratio determination. The physiological property may comprise the concentration of hemoglobin, lipid, water, oxygen or other molecules capable of absorbing light and combination thereof.

There is further provided a method for characterizing an abnormality in a tissue the method comprising analyzing the tissue with a modality other than optical imaging, identifying, based on the modality, one or more abnormal regions, obtaining a value related to an optical property of the abnormal regions, deriving a physiological property value from the optical property of the abnormal regions, and characterizing the abnormal regions based on the derived physiological property value.

In another embodiment of the invention there is also provided a method for establishing a diagnosis of an abnormality within a tissue the method comprising obtaining a first diagnosis of the abnormality with a modality other than optical imaging, determining, based on the first diagnosis, one or more feature of the abnormality to be characterized by optical imaging of the abnormality, obtaining an optical image of the tissue comprising the abnormality, identifying the abnormality within the optical image and characterizing the feature, by measuring one or more physiological property.

Thus, in a broad embodiment, the method of the present invention advantageously provides functional characterization of biological tissues that can be used for diagnosis purposes.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION OF THE PREFERRED EMBODIMENT

Figure 1:
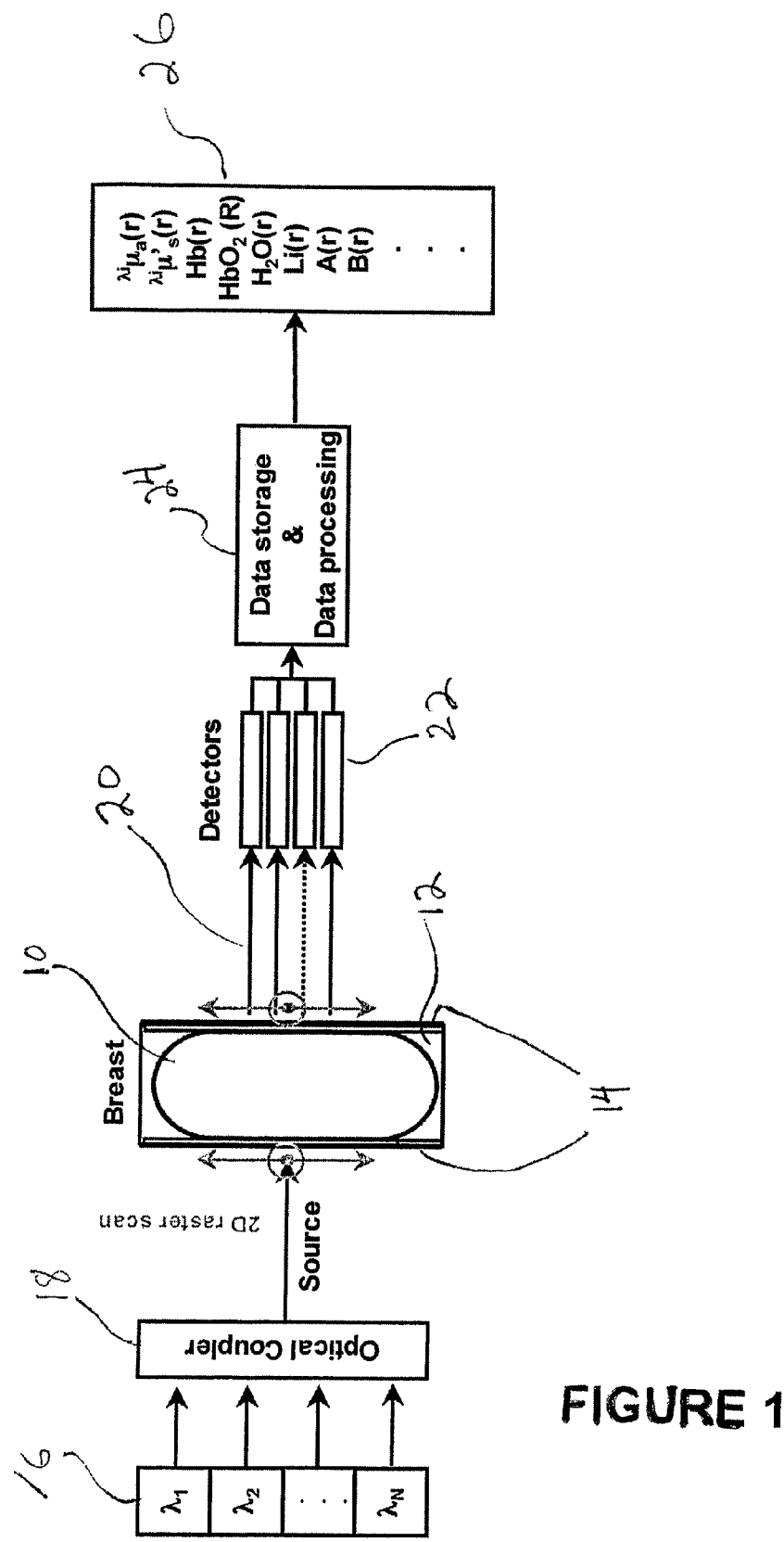
FIG. 1 is a schematic diagram of an embodiment of the optical system used to acquire optical data.

Light propagation in tissue is well modeled by the diffusion equation. In the time domain the mathematical expression modeling light propagation in a homogeneous medium is:

$$\frac{1}{v}\frac{\partial}{\partial t}\Phi(r, t) - D\nabla^2\Phi(r, t) + \mu_a\Phi(r, t) = S(r, t), \quad (1)$$

where $\Phi(r,t)$ is the photon flux, $D=\frac{1}{3}\mu_s'$ is the diffusion coefficient expressed with $\mu_s'$ being the scattering coefficient, $\mu_a$ is the linear absorption coefficient, v is the speed of light in the medium and $S(r,t)$ is the source term (assumed to be a $\delta$-function in our case). The temporal data acquired from a scan can be processed with diffuse optical spectroscopy (DOS) and diffuse optical tomography (DOT). Many studies have been dedicated to solving equation (1) for diverse geometries. Delfino et al. (Delfino et al. Appl. Opt. (1999); 38:4228-4236) suggested that, in the case of transmittance, the expression provided by Contini et al. (Contini et al. Applied Optics (1997); 36:4587-4599) results in the most satisfactory agreement between experimental and theoretical predictions. In one embodiment of the present invention, the expression from Contini et al. is used:

$$T(\rho, t) = \frac{\exp\left(-\mu_a vt - \frac{\rho^2}{4Dvt}\right)}{2(4\pi Dv)^{3/2}t^{5/2}} \sum_{m=-\infty}^{+\infty}\left[z_{1,m}\exp\left(-\frac{z_{1,m}^2}{4Dvt}\right) - z_{2,m}\exp\left(-\frac{z_{2,m}^2}{4Dvt}\right)\right], \quad (2)$$

where $T(\rho,t)$ represents the probability that a photon, entering the medium at t=0, exits at a time t and at a distance $\rho$ per unit of time and unit of area. $Z_{1,m}$ and $Z_{2,m}$ are expressed by:

$$\begin{cases} z_{1,m} = s(1-2m) - 4mz_e - z_o, \\ z_{2,m} = s(1-2m) - (4m-2)z_e + z_o \end{cases} \quad (3)$$

$$m = (0, \pm 1, \pm 2, \ldots); z_o = \frac{1}{\mu'_s},$$

and account for the boundary conditions. The reader is referred to Contini et al. Applied Optics (1997); 36:4587-4599 incorporated herein by reference, for more insight into the derivation of the transmittance function.

The theoretical expression of equation (2) is used in an inverse problem to retrieve the bulk optical properties of the medium under investigation. In this fitting algorithm, a least squares fit was performed with three free parameters: the amplitude of the temporal point spread function (TPSF), the absorption coefficient and the scattering coefficient. The best fit was reached iteratively with a Levenberg-Marquardt algorithm and minimization of a $\chi^2$ merit norm.

The absorption and scattering coefficients estimated through this procedure are related to the physiological and structural bulk properties of the biological tissue probed. The absorption coefficient is related to the different constituents of the breast through the linear contributions of the different tissue chromophores:

$$\mu_a(\lambda) = \sum_i^{NC} \varepsilon_i^\lambda C_i \quad (4)$$

where $\varepsilon_i^\lambda$ is the wavelength dependent extinction coefficient of the $i^{th}$ chromophore and $C_i$ its concentration. In the case of breast tissue, it is widely assumed that the primary NIR absorbers are oxyhemoglobin, deoxyhemoglobin, hemoglobin, water and lipids (denoted as $HbO_2$, Hb, $H_2O$ and Li respectively). $HbO_2$ and Hb can be combined to obtain blood volume (HbT) and blood oxygen saturation ($SaO_2$). It will be appreciated that other NIR chromophores (absorbers) can be present and that the composition of NIR chromophores may vary from tissue to tissue.

The scattering coefficient originates mainly from the refractive index micro-variations in tissue. It has been shown that a simple Mie-scattering approximation is applicable to scattering of breast tissue (Durduran et al. Phys Med Biol. (2002); 47:2847-2861):

$$\mu_s'(\lambda) = a\lambda^{-b} \quad (5)$$

where a is referred to as scattering amplitude and b as scattering power. These last parameters are related to the breast composition. Typically, large scatterers have lower a and b values, whereas small scatterers have higher a and b (Mourant et al. Appl. Opt. (1997); 36:949-957). Moreover, Cerrusi et al. (Cerrusi, Acad. Radiology 2001; 8:211-218) show a linear relationship for both the lipid and water content to the scattering power. This relationship was established experimentally from a study based on 28 women and with a coefficient of determination $r^2$ of 0.84 for the lipid content and 0.85 for the water content. This relationship is expressed as:

$$[H_2O] = 0.35 \cdot b - 0.05(\%)$$

$$[Li] = -0.50 \cdot b + 0.90(\%) \quad (6)$$

The accuracy of the time resolved technique can be used to obtain absolute values of the scattering coefficient to estimate the lipid bulk concentrations from equation (6). Then the inverse problem expressed in equation (4) is reduced to three chromophores and hence far better conditioned.

To solve equation (4) a non-negative least squares (NNLS) algorithm was used. The initial value of the water concentration was provided by equation (6) but set as a free parameter in the fitting algorithm. The absorption coefficients fed to the NNLS algorithm were corrected for the lipid contribution at each wavelength. This contribution was small as expected for the wavelengths used in the present method.

It is also possible from multiple spatial measurements to estimate the local distribution of the absorption and scattering coefficients. The concept of this application is to employ measurements recorded from tissue using multiple optical source—detector pairs and retrieve (reconstruct) the object function by synthesizing the measurements through solution of an inverse problem (Arridge. Inverse problems (1999); 15:R41-R93).

One cost-efficient and robust approach to perform Diffuse Optical Tomography (DOT) is to solve the heterogeneous equation within the Rytov perturbative approach (O'Leary. PhD University of Pennsylvania 1996). In the case of time resolved measurements, there are potentially different types of data sets. We chose to select the $0^{th}$ moment (equivalent to continuous mode) and $1^{st}$ moment (mean time of photon arrival) of the TPSF (Arridge. Inverse problems (1999); 15:R41-R93). The preferred embodiment involves reconstructing only for perturbation in the absorption coefficient and thus the scattering coefficient was assumed to be homogeneous over the reconstructed volume. The DOT problem is thus expressed as:

$$\begin{bmatrix} \Phi_{sc}^{(l)}(r_{sd1}) \\ \vdots \\ \Phi_{sc}^{(l)}(r_{sdm}) \\ \Phi_{sc}^{(MT)}(r_{sd1}) \\ \vdots \\ \Phi_{sc}^{(MT)}(r_{sdm}) \end{bmatrix} = \begin{bmatrix} W_{11}^{(l)} & \cdots & W_{1n}^{(l)} \\ \vdots & \ddots & \vdots \\ W_{m1}^{(l)} & \cdots & W_{mn}^{(l)} \\ W_{11}^{(MT)} & \cdots & W_{1n}^{(MT)} \\ \vdots & \ddots & \vdots \\ W_{m1}^{(MT)} & \cdots & W_{mn}^{(MT)} \end{bmatrix} \begin{bmatrix} \delta\mu_a(r_1) \\ \vdots \\ \delta\mu_a(r_n) \end{bmatrix} \quad (7)$$

where $$\Phi_{sc}^{(l)}(r_{sdi}) = \ln\left(\frac{U(r_{sdi})}{U_0(r_{sdi})}\right)$$

is the $0^{th}$ moment Rytov pertubation, $\Phi_{sc}^{(MT)}{}_{sdi} = \bar{t}(r_{sdi}) - \bar{t}_0(r_{sdi})$ the $1^{st}$ moment Rytov perturbation, with $W_{ij}^{(l)}$ and $W_{ij}^{(MT)}$ the corresponding weight of the sensitivity matrix. The expressions for the weight functions are:

$$W_{ij}^{(l)} = \frac{1}{(4\pi D)^2 r_{sivj} r_{vjdi}} \cdot \exp\left[-\sqrt{\frac{\mu_a}{D}} \cdot (r_{sivj} + r_{vjdi})\right] \cdot \frac{1}{U_0(r_{sdi})} \quad (8)$$

$$W_{ij}^{(MT)} = \frac{(r_{sivj} + r_{vjdi})}{c \cdot \sqrt{\mu_a \cdot D} \, (4\pi D)^2 r_{sivj} r_{vjdi}} \cdot$$

$$\exp\left[-\sqrt{\frac{\mu_a}{D}} \cdot (r_{sivj} + r_{vjdi})\right] \cdot \frac{1}{U_0(r_{sdi})} - \left(\frac{\bar{t}_0(r_{sdi}) \cdot W_{ij}^{(l)}}{U_0(r_{sdi})}\right)$$

with $r_{sivj}$ and $r_{vjdi}$ di corresponding to the $i^{th}$ source-$j^{th}$ voxel and $j^{th}$ voxel-$i^{th}$ detector distances, respectively, and $U_0(r_{sdi})$ and $\bar{t}_0(r_{sdi})$ correspond to the homogeneous $0^{th}$ moment and $1^{st}$ moment of the TPSF for the considered source detector-pair.

In one embodiment of the present invention, the optical data can be acquired in transmission geometry and processed as described above to obtain optical properties of the medium. A schematic representation of the system is shown in FIG. 1. The medium 10 to be investigated is positioned in a tank 12 and stabilized with stabilization plates 14, which can be made of Plexiglas that are part of the frame of the tank. The tank is filled with matching liquid to ensure that the diffuse light detected will be within the optimal dynamic range of the system. Light 16 of a selected wavelength is directed to the object 10 via an optical coupler 18 and transmitted light is collected by a detection array optical system 20, which may be comprised of lens-coupled multimode fibers that form an X constellation. The fibers are preferably placed in transmittance geometry relative to the emission fiber, with the central detection fiber aligned with the emission fiber. However it will be appreciated that a reflection geometry could also be used to characterize the optical properties of the medium. The other tips of the detection fiber are facing a detector 22, such as a streak camera (C5680-34S from Hamamatsu Corporation, Bridgewater, N.J., USA).

The optical data thus obtained are stored and processed in a data storage and processing unit 24. The result of the processing yields information on the optical and physiological properties 26 of the medium.

In one embodiment, a Softscan® instrument (Advanced Research Technologies Inc., St-Laurent, Qc, Canada) may be used and is described in Intes et al. Proc SPIE 2004; 5578: 188-197, which is incorporated herein by reference. The light source is a TiSaphire laser MaiTai from Spectra-Physics (Spectra-Physics, Mountain View, Calif.) driven at 80 MHz. The output of the Mai Tai laser is sent to an optical isolator that is used to reduce back reflections into the laser cavity. Its output is then coupled, by means of a fiber port, into a (1×2) coupler/splitter having 62.5 um core diameter fibers with an NA of 0.275 at each port. The Mai Tai laser power is then controlled using a fibered-motorized-variable (blocking type attenuator) having the same input and output fiber characteristics previously mentioned. The output is split at a 90/10 ratio (typically) and the 90-output is sent to the input collimator fiber going to the patient interface. The motorized optical attenuators allow monitoring of the power injected in the tissue in order to control the Maximum Permissible Exposure (MPE) during a clinical scan. The Softscan® platform is a class IV system.

The emission fiber and the detection array are raster scanned simultaneously over the region of examination. The scan is performed continuously and the data is averaged every 5 frames at a rate of 1 mm translational displacement per frame (the camera acquire 30 frames/second). The data can be collected at one or several wavelengths. In a preferred embodiment four discrete wavelengths are collected. A typical examination investigates an 80 mm by 95 mm area leading to 1520 spatial points for each wavelength. In this prototype, the system gathered information at 760, 780, 830 and 850 nm. The spectral range allowed by the MaiTai and the streak camera drove the choice of the wavelengths (750 to 850 nm). A wavelength optimization procedure based on the condition number of the extinction coefficient matrix of the principal chromophores of the breast, led to the choice of the above-mentioned discrete set of wavelengths (see for example international patent publication WO 2004/06426, published on Aug. 5, 2004, incorporated herein by reference). This procedure is akin to the one described in Corlu A. et al. Opt. Left. (2003); 28:2339-41.

The gathered data consist of Time Point Spread Functions (TPSF) acquired with a 10 ps resolution within a 4 ns time window. Among the critical aspects of the time resolved system are the drift (<5 ps/h) and the jitter (2 ps) (Ntziachristos et al. Med Phys. (2001); 28:1115-1124).

The inverse problem was performed using an algebraic reconstruction technique (ART) (Intes et al. Phys. Med. Biol. (2002); 47:N1-N10). For all the reconstructions herein, the relaxation parameter was fixed to 0.1 and the number of iterations fixed to 200. These last parameters were selected through phantom reconstructions studies.

Besides hardware validation, the system performance was also validated through laboratory experiments. These experiments aimed to qualify the performance of the platform for DOS and DOT applications in optical mammography.

The performance of the prototype was evaluated through phantom experiments. The first experiments aimed to characterize the ability of the platform to recover absolute homogeneous optical coefficients. For this purpose, spectroscopic experiments using a liquid model were carried out to evaluate the system's ability to accurately retrieve the absolute absorption and scattering coefficients. The liquid phantoms are suspensions of Lyposin II 10%® (Abbott Laboratories, Ltd., Montreal, Canada) intravenous fat emulsion and India ink diluted in de-mineralized water.

Figure 2:
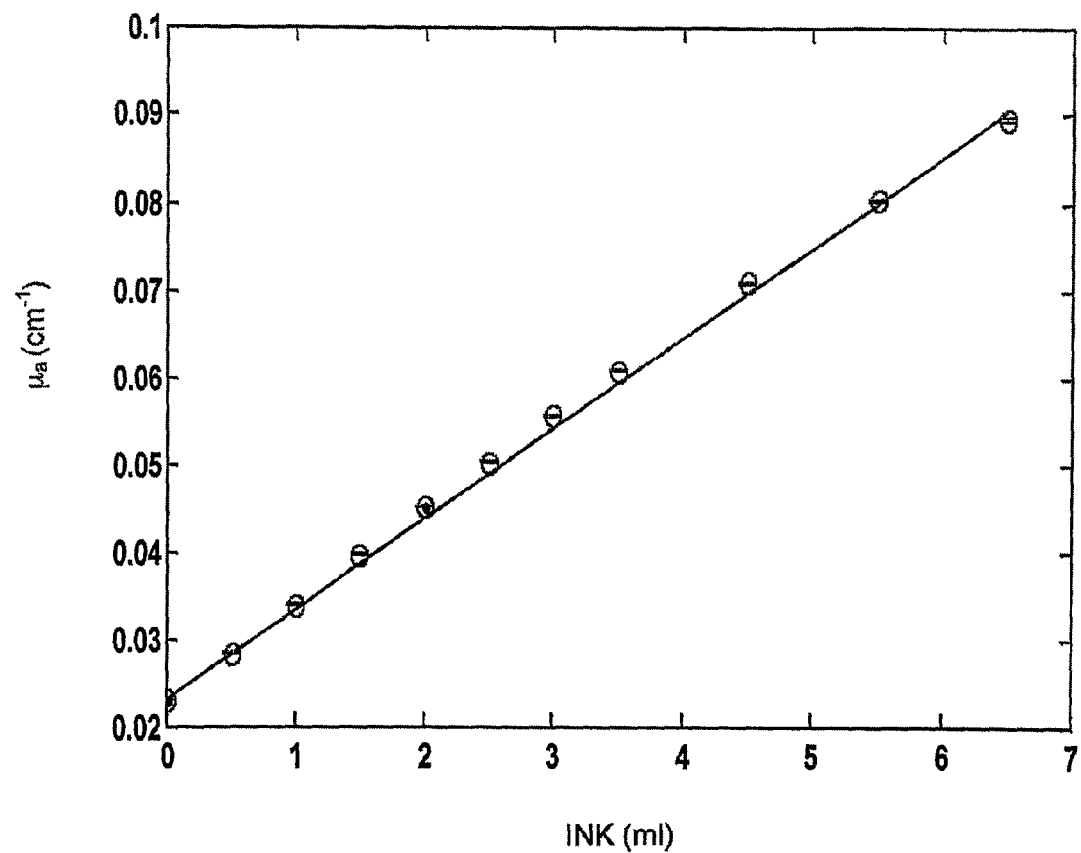
FIG. 2 is a plot of an absolute absorption estimation of India ink in which the markers correspond to the estimated absorption values with the standard deviation computed from 10 measurements and the line corresponds to the expected absorption values.

Lyposin solution was used to simulate a scattering background $\mu_s'=7$ cm$^{-1}$ at 780 nm. Adding a small amount of India ink gave rise to changes in the absorption. The ink extinction coefficients were measured with a spectrometer (Ocean Optics) and were used to calculate the expected absorption values. Results are displayed in FIG. 2. The optical coefficients were chosen to match the range of optical properties of human breast tissue with and without contrast agent (Intes et al. Medical Physics (2003); 30:1039-1047).

The measurements were repeated 10 times at the same spatial location for each titration. The maximum standard deviation in the absorption coefficient observed for titrations across the four wavelengths was 1.23%. The maximum deviation of the estimated absorption coefficient to the expected one was 3% over the whole titration range (the zero ink point was calibrated to the water value). The scattering parameter was estimated to be $\mu_s'=6.5$ cm$^{-1}$ at 780 nm, which corresponds to a ~7.5% decrease compared to the expected value. A cross talk was observed between the scattering coefficient and the absorption titration. The scattering coefficient was decreasing with increases in absorption with a maximum change of 5% for the extreme scattering points.

Figure 3:
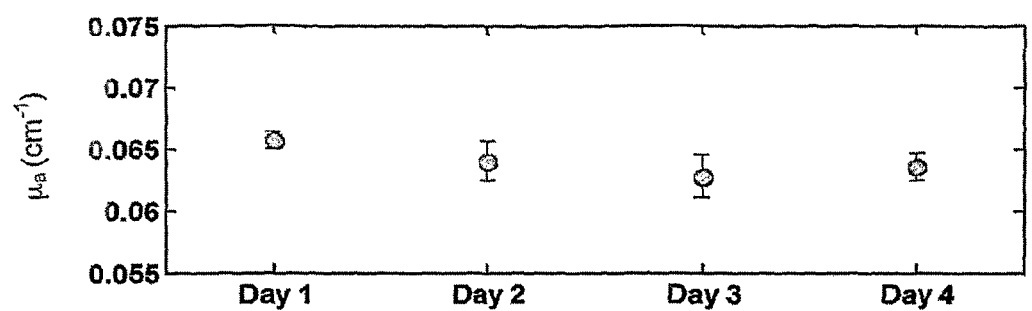
FIG. 3 are plots of the absolute optical properties estimated over four days. The results for 780 nm are presented here.

Secondly, the ability of the platform to provide repeatable optical parameters was assessed through solid phantom studies. The solid phantom was preferred to the liquid due to the variation of optical properties encountered form batch to batch in the Lyposin solution. The solid phantoms are constructed from a mixture of polyurethane, NIR dye and TiO$_2$ particles. In this study we used two phantoms referred to as EASY-T and HARD-T. The phantoms are identical in size and optical properties, except that the absorptive inclusion is at a different location in each. EASY-T bears an absorptive inclusion 0.7 cm from the surface and HARD-T an inclusion buried in the middle. To test the repeatability of the absorption and scattering measurements, these phantoms were scanned over an area away from the boundaries and away from the inclusions. The test was repeated over four consecutive days. Each day, the system was powered up and allowed 1 h to warm up prior to scanning. The system was switched off at the end of each day. An example of the optical properties recovered is presented in FIG. 3.

The mean and standard deviation were computed over nine different spatial acquisitions within a 1 cm×1 cm ROI on the phantom. The maximum standard deviation observed on any given day was found to be ~1% for the absorption coefficient and ~0.5% for the scattering coefficient. The maximum standard deviation of the per-day means (cf. Table 1) was about 3.3% at 830 nm and 850 nm for the absorption coefficient and ~1.55 at 760 nm for the scattering coefficient.

TABLE 1

Mean optical properties estimated over four days with the corresponding standard deviation computed from nine spatial points acquired each day over a four day period.

|  | 760 nm | 780 nm | 830 nm | 850 nm |
|---|---|---|---|---|
| $\mu_a$ (cm$^{-1}$) | 0.070 ± 7.72E−04 | 0.064 ± 4.59E−04 | 0.0294 ± 2.95E−05 | 0.027 ± 1.59E−04 |
| $\mu'_s$ (cm$^{-1}$) | 8.86 ± 4.40E−02 | 8.64 ± 2.27E−02 | 8.62 ± 4.77E−03 | 8.55 ± 1.59E−02 |

Figure 4:
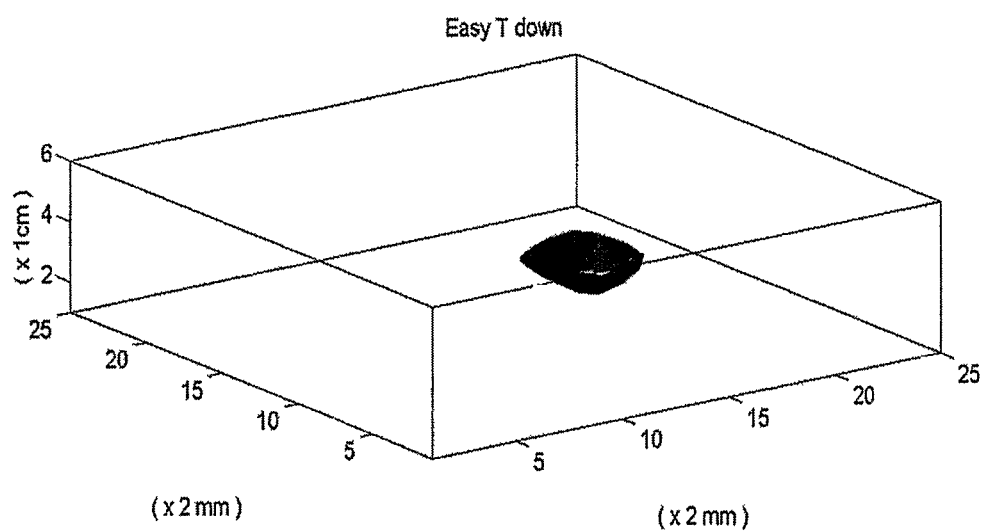
FIG. 4 is an example of reconstruction according to the preferred embodiment, including Easy-T with the inclusion close to the source and in which the iso-surfaces were defined at 50% of the maximum of the reconstructed absorption.
Figure 5:
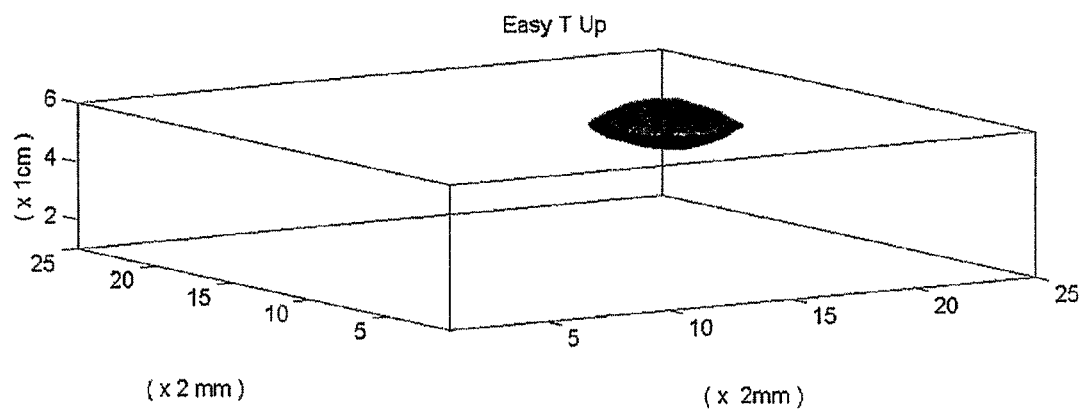
FIG. 5 is an example of reconstructions according to the preferred embodiment, including Easy-T with the inclusion close to the detectors in which the iso-surfaces were defined at 50% of the maximum of the reconstructed absorption.
Figure 6:
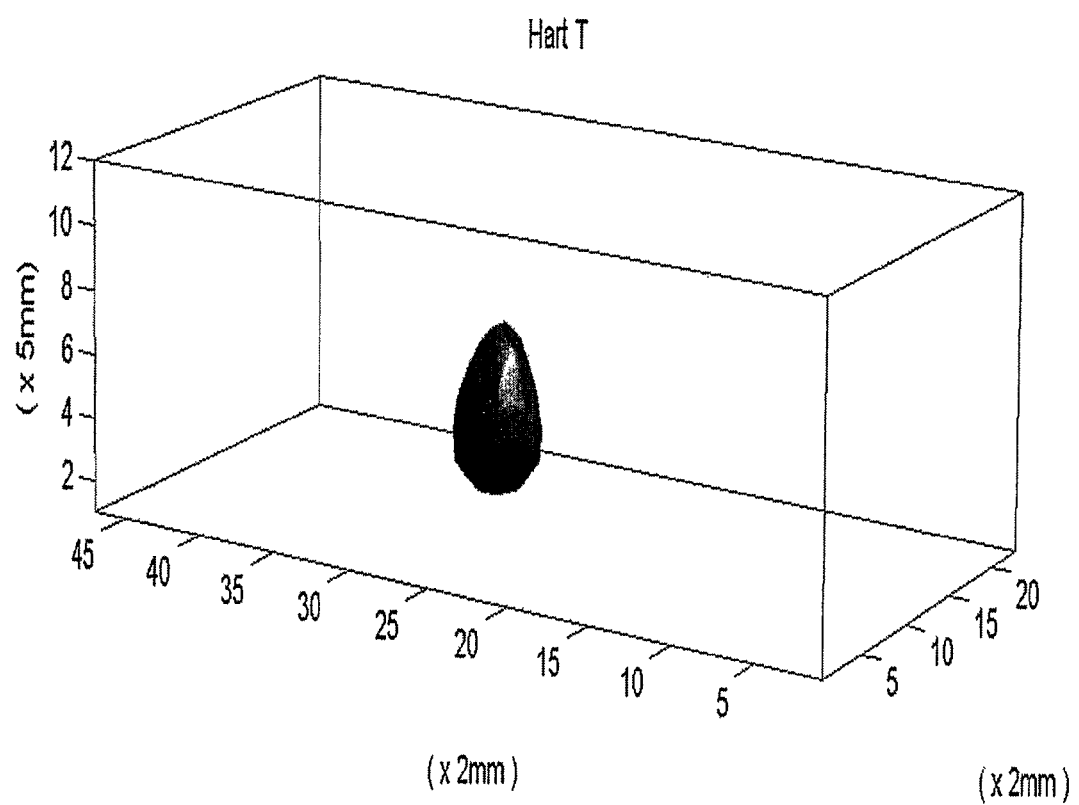
FIG. 6 is an example of reconstructions according to the preferred embodiment, including Hard-T in which the iso-surfaces were defined at 50% of the maximum of the reconstructed absorption.

The system's ability to recover local absorption contrast was also investigated through phantom studies. The studies were based on the same phantoms described above. Both phantoms bear inclusions of 2:1 contrast in absorption and 1 cm$^3$ in volume. The reconstructions were performed according to the method described above. Examples of reconstructions are provided in FIG. 4-6. The figures are displayed in terms of iso-surfaces.

In all the cases, the inclusion was reconstructed successfully. The locations of the inclusions were well recovered. In the case of EASY-T the volume reconstructed was in agreement with the expectation. In the case of HARD-T, the inclusion was more diluted in terms of depth estimation. It is well known that the central slices in transmittance geometry are the more difficult to reconstruct accurately and due to a limited number of tomographic views, the inclusion is elongated in depth.

While optical data acquisition has been described as applied to time domain (TD), it will be appreciated that frequency domain (FD) acquisition may also be used to recover optical parameters such as $\mu_a$ and $\mu'_s$. Algorithms for reconstruction in FD are well known in the art (Sevick-Muraca et al., Neoplasia 2: 388-417, 2000, incorporated herein by reference).

In one embodiment of the invention, the optical properties of biological tissues are exploited to detect the presence of abnormalities. Biological tissues well known in the art and examples as they relate to humans include breast tissue, muscles, brain, cartilage and the like. The ratio of the values of an optical property such as the absorption coefficient or the scatter coefficient obtained from different regions of the tissue can be used to map variations within the tissue. The ratios obtained from the pair-wise comparison of different regions may also be compared to known ratios of abnormal to normal tissue.

The optical property can be used to derive physiological properties such as the concentration of molecules present in the tissue. In a preferred embodiment the ratio of a value of physiological property can be used to detect the presence of an abnormality. By physiological property it is meant any physiological characteristic of a tissue that can be measured using optical methods. Such physiological properties may include the concentration of any optically detectable chromophore including fluorophores. Molecules that can provide physiological information for a tissue include but are not limited to oxy-hemoglobin, deoxy-hemoglobin, total hemoglobin, oxygen saturation, water content and the like. The ratios of several physiological characteristics obtained from the comparison of different regions of a tissue may be combined to increase the reliability of the detection of an abnormality.

It will be appreciated that the ratios between the different locations may be obtained without prior knowledge of the presence of an abnormality. However, in another embodiment of the invention, an optical image of the tissue can first be obtained and any suspicious and normal regions can be identified based on the image. Ratios of physiological property or optical property values between these regions can then be obtained to confirm whether suspicious regions are abnormal.

In yet another embodiment of the invention, it is also possible to identify the abnormality with a modality other than optical imaging and the abnormality can then be characterized optically using the method described above. For example, an abnormality may be identified using X-ray imaging and its location may be registered within an optical image of the tissue. Ratios of optical or related physiological properties may then be obtained between the abnormal and normal regions so identified. The modalities may include imaging modalities other than optical imaging but may also include non-imaging modalities such as physical examination or sample testing including blood test, microbiological testing and the like. Imaging modalities may include but are not limited to X-ray, Magnetic Resonance Imaging, Positron Emission Tomography, ultra-sound and the like. It will be appreciated that the results from multiple modalities may be combined.

Optical characterization of an abnormality may provide useful physiological information for medical diagnosis. Thus the comparison of physiological properties between normal tissue and an abnormal region within the tissue can provide information indicative a disease state.

The tissue being analyzed may be in vivo tissue, that is to say tissue that is part of an individual, but the characterization may also be performed ex-vivo, that is to say on tissue that has been removed from an individual.

A prospective breast tissue study was performed under the supervision of Dr. David Fleiszer at the Cedars Breast Center of the Royal Victoria Hospital in Montreal, Quebec, Canada. During this study, 65 women with either abnormal or normal mammograms were enrolled under Protocol 2002-01 ("Validation of design changes on Softscan® system performance and evaluation of image reconstruction algorithm"). Demographic information was collected including: age, body mass index (BMI), bra size (cup size), breast thickness, radiographic density and hormonal status. Subjects with abnormal mammograms underwent biopsy after the Softscan® procedure.

Due to technical modifications occurring during the time of the study or to optical examinations non-relevant to this work, the analysis was limited to a sub-set of 52 subjects. Twenty-four of these women were post-menopausal, 14 were pre-menopausal, 1 was currently going through menopause and 13 had had a hysterectomy. Fifteen of the post-menopausal subjects had previously taken or were at that time taking some form of hormone replacement therapy. The subject population enrolled during this protocol represents a reasonable cross-section of demographic factors.

TABLE 2

Main demographics parameters of the recruited population (N = 49). The thickness corresponds to the distance between the stabilization plates after soft compression of the breast.

|  | Minimum | Maximum | Mean | Std Deviation |
|---|---|---|---|---|
| Age (yr.) | 24 | 80 | 57.2 | 13.7 |
| BMI (kg/m$^2$) | 15.9 | 48.7 | 27.2 | 6.2 |
| Thickness (cm) | 3.0 | 8.5 | 5.7 | 0.96 |

A clinical research nurse assessed the subject's breast before and after the Softscan® procedure to evaluate for any changes. There was also a 24-hour follow-up call to ensure that the subjects had not undergone any changes since the Softscan® procedure. According to a preferred embodiment of the invention, the Softscan® procedure was performed with the subject lying on a cushioned table in the prone position with the pendulous breast stabilized between the plexiglass plates of the aquarium (cf. FIG. 1). The ROI (region of interest) was then identified using the mammograms and the patient positioned accordingly. Optical compensation liquid was added into the aquarium (comprised between the plates 14) having characteristics that mimic the optical properties of the human breast ($\mu_a$=0.051 cm$^{-1}$ and $\mu_s'$=11 cm$^{-1}$ at $\lambda$=780 nm). The optical imaging scan followed next. The first part of the optical imaging consisted of a fast, high-resolution (2 mm step size), one wavelength, reconnaissance scan. By displaying the absorbance picture of the ROI probed in near real time allowed to assess the appropriate positioning of the breast. Secondly, a 5 mm step size with a four-wavelength scan was performed. The data of this last scan were processed off-line to provide the physiological parameters described below. Overall, the Softscan® procedure required approximately 1 hour.

While in the present case the ROI was determined based on the X-ray mammogram, the method of the present invention may also be performed without prior knowledge of the presence of an abnormality within the tissue. In fact, in one aspect of the invention there is also provided a method for detecting the presence of an abnormality using optical data.

The bulk optical properties derived from the population enrolled in this study were investigated. Among the 52 patients data set, 49 patients were retained. For three cases, the data was either not available or technical difficulties occurring during the optical examination led to poor data quality. For all the cases in the 49-subset, a 'healthy' tissue ROI was defined in accordance with prior information. This prior knowledge consisted of an X-Ray mammogram, palpation information and digital pictures of the compressed breast taken by the nurse prior to filling the tank with the matching liquid. The selection of the ROI was performed during consensus meetings including personnel with extended experience in X-Ray diagnosis. The ROI was carefully defined such that suspicious areas and matching liquid were not taken into account and thus did not corrupt the 'healthy' optical properties. The average optical properties of the 'healthy' ROI were derived by DOS for each wavelength and each of the 49 subjects as described above. The descriptive statistics of the average optical properties are provided in Table 3.

The optical properties described in Table 3 are consistent with previously published data (Cerussi et al. Biophotonics 2003, dec:38, Grosenick et al. Appl. Optics 2003; 42: 3170, Durduran et al. Phys Med Biol. (2002); 47:2847; Susuki et al. J Biomed Opt. 1996; 1:330; Shah et al. PNAS 2001, 98:4420; Spinelli et al. J. Biomed Opt. 2004, 9:1137). The data presented in Table 3 define the bounds of the platform specifications in terms of dynamical range. The dispersion of the average optical properties depicts the difference in the breast composition in the population. This can be seen with the estimated physiological parameters of the population.

Figure 7:
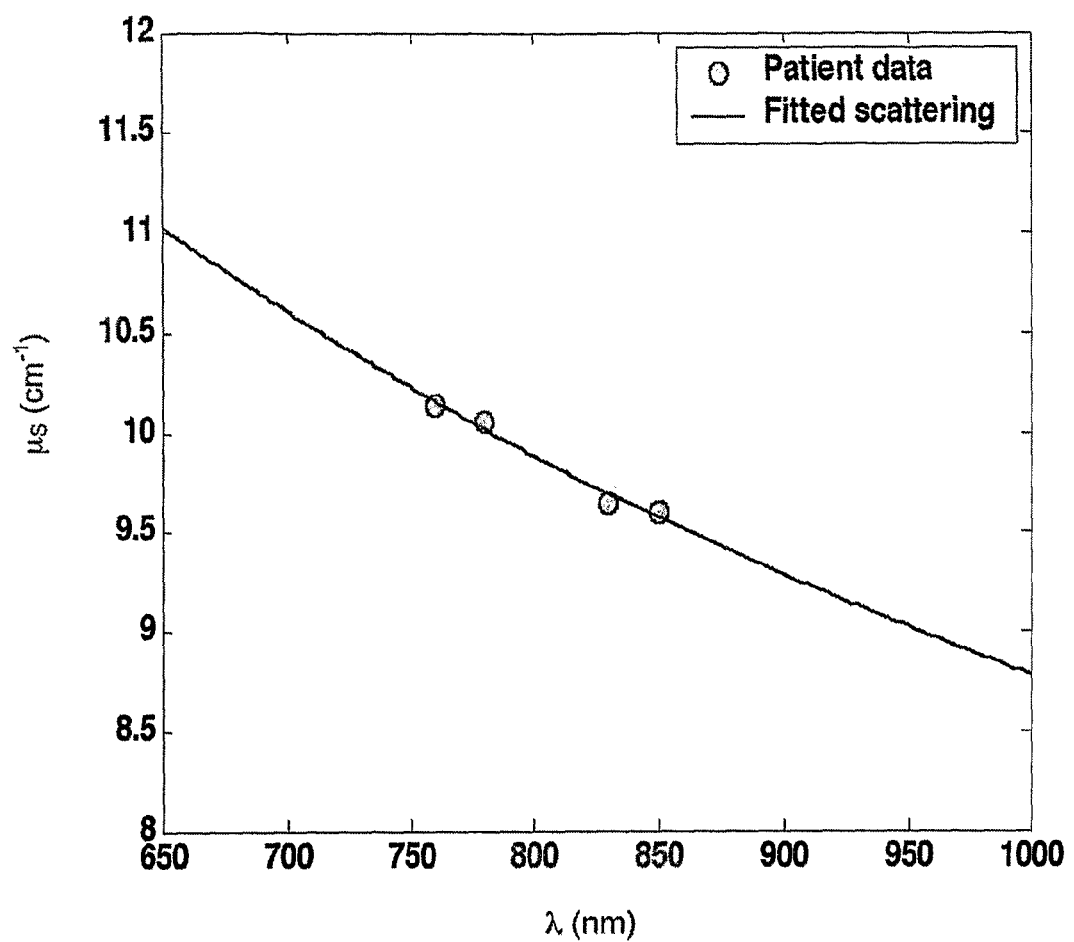
FIG. 7 is a plot showing an example of scattering fitting results for patient #31 in which the extinction coefficients of $HbO_2$, $Hb$ and $H_2O$ were obtained from Scott Pralh's web page (http://omlc.ogi.edu/staff/prahl.html) and the lipid extinction coefficient was kindly provided by Turgut Durduran (Durduran et al. Phys Med Biol. (2002); 47:2847-2861)
Figure 8:
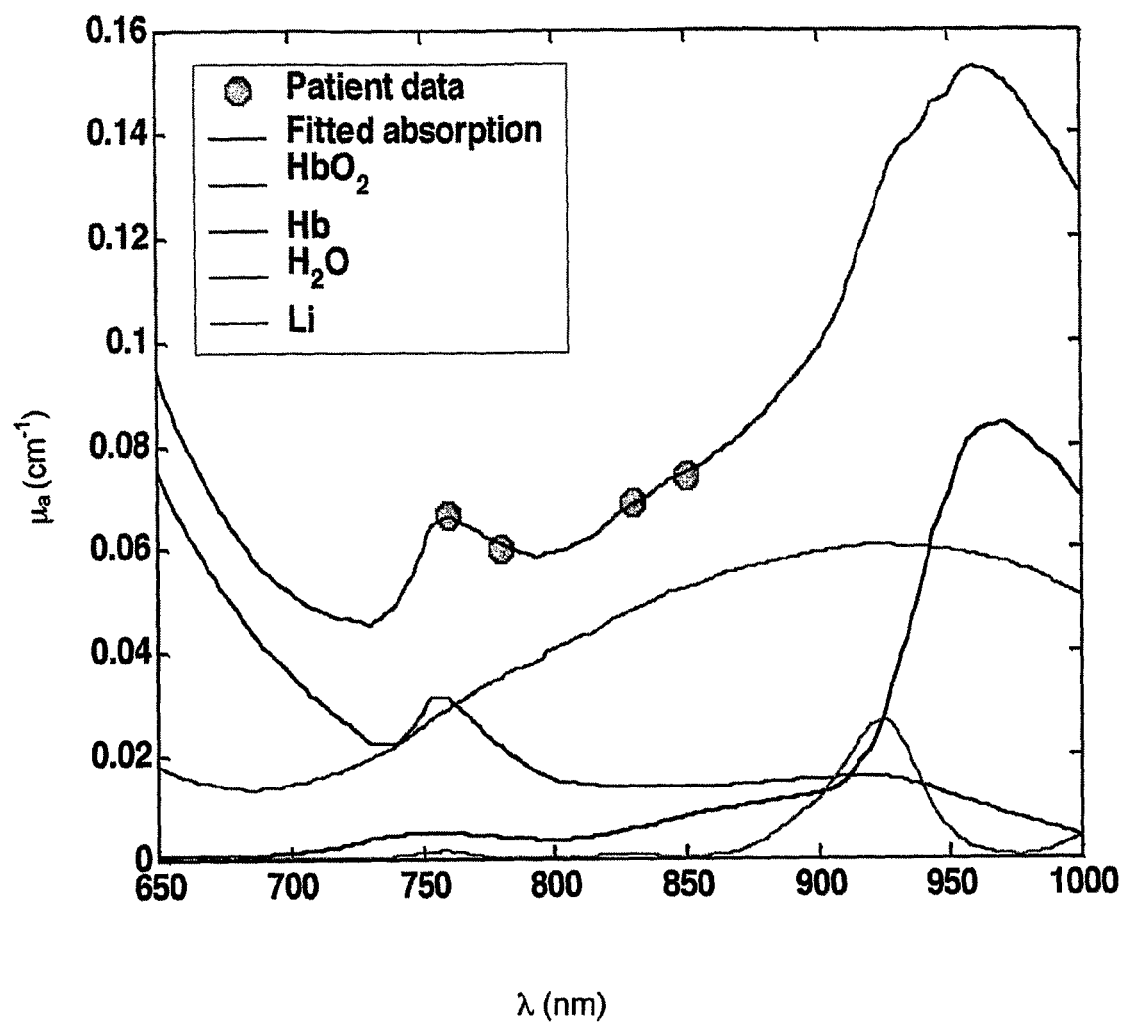
FIG. 8 is a plot showing an example of absorption fitting results for patient #31 in which the extinction coefficients of $HbO_2$, $Hb$ and $H_2O$ were obtained from Scott Pralh's web page (http://omlc.ogi.edu/staff/prahl.html) and the lipid extinction coefficient was kindly provided by Turgut Durduran (Durduran et al. Phys Med Biol. (2002); 47:2847-2861)
Figure 9:
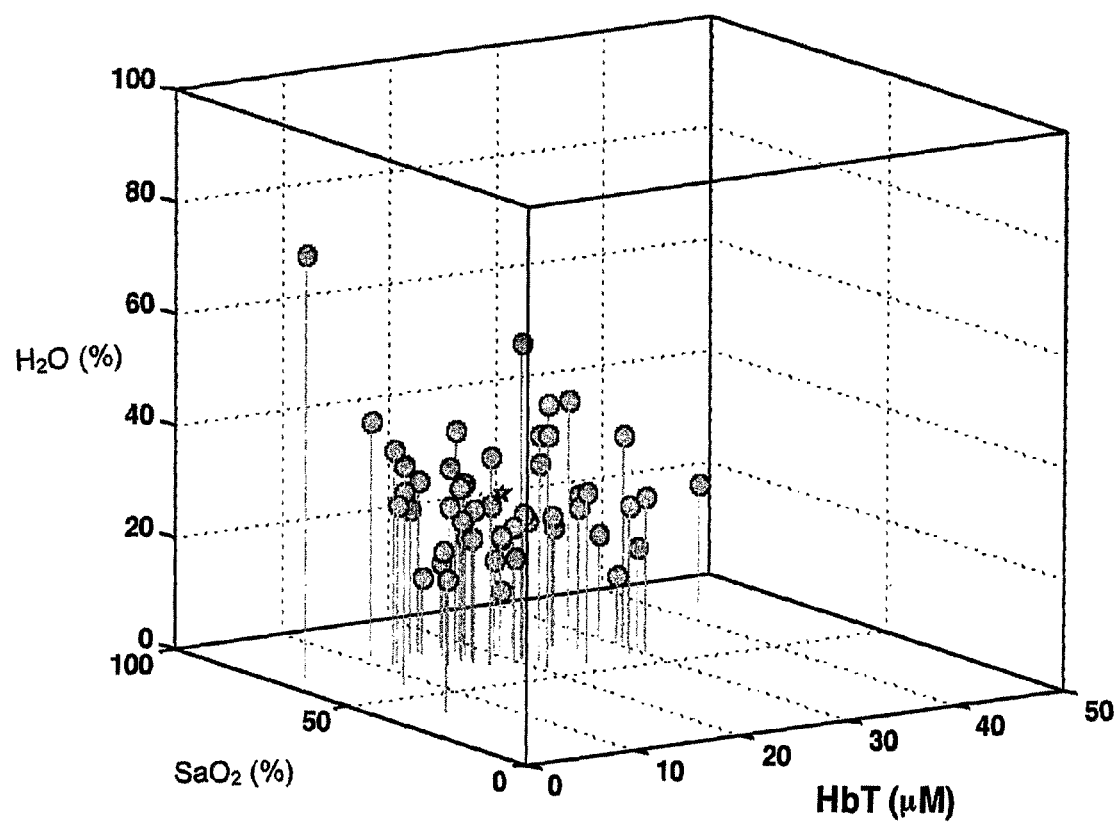
FIG. 9 is a plot showing Chromophore concentrations estimated by NNLS in which the pentagrams correspond to the mean values as given in Table 3.
Figure 10:
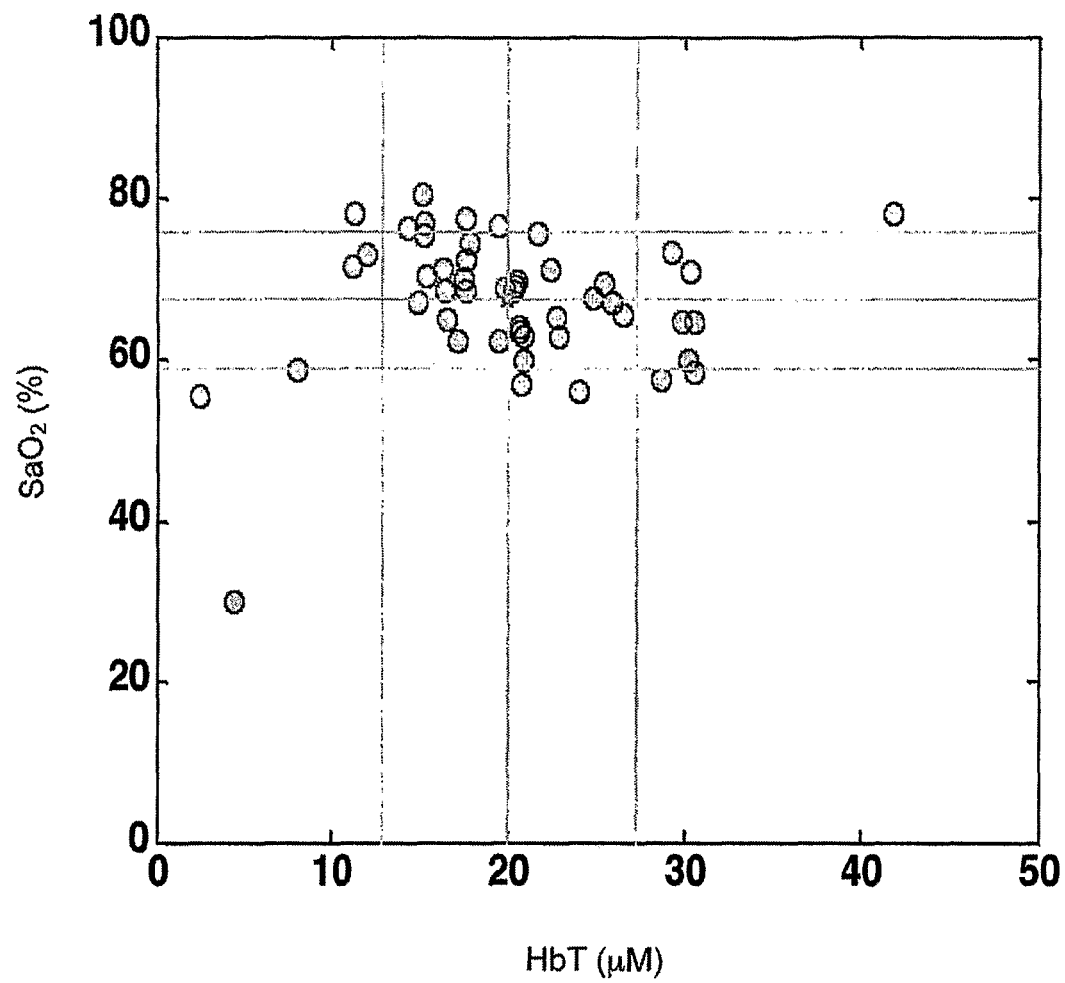
FIG. 10 is a plot showing $SaO_2$ versus $HbT$ for the 49 cases in which the dotted line indicates the mean and standard deviation as given in Table 3.
Figure 11:
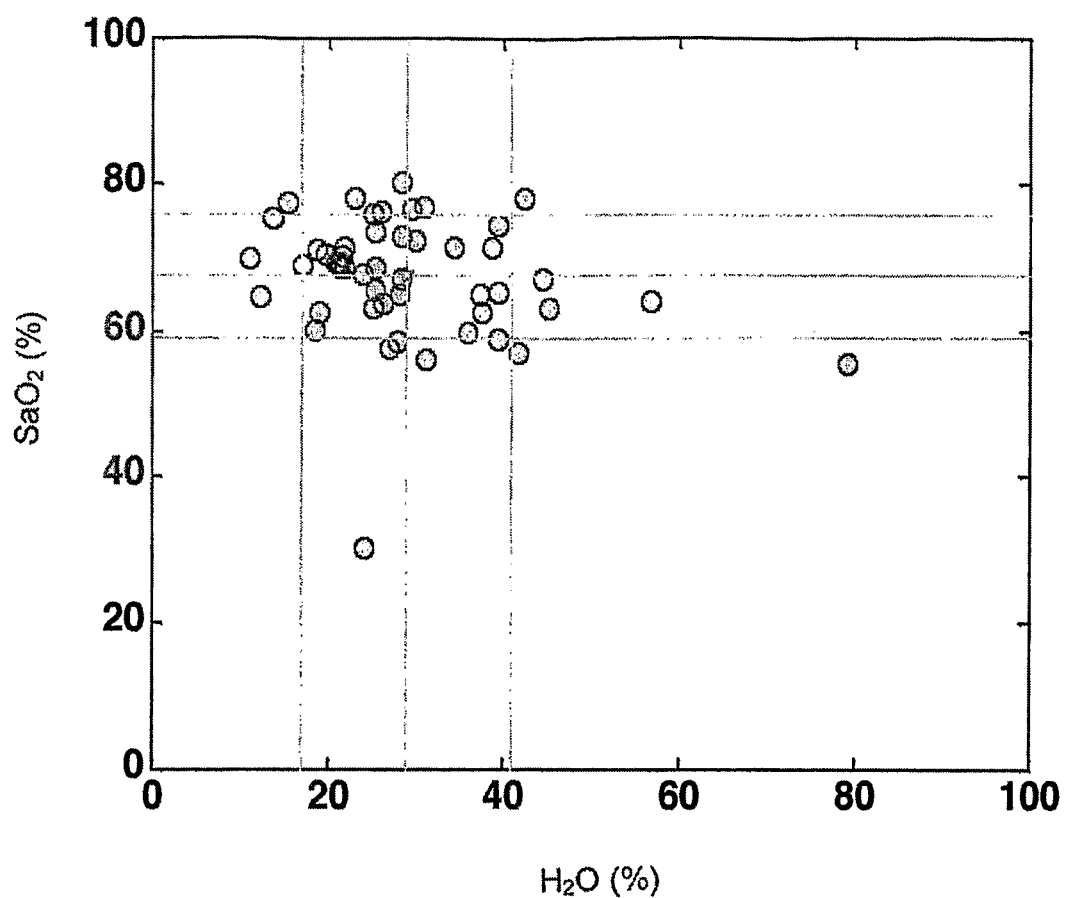
FIG. 11 is a plot showing $SaO_2$ versus $H_2O$ for the 49 cases.
Figure 12:
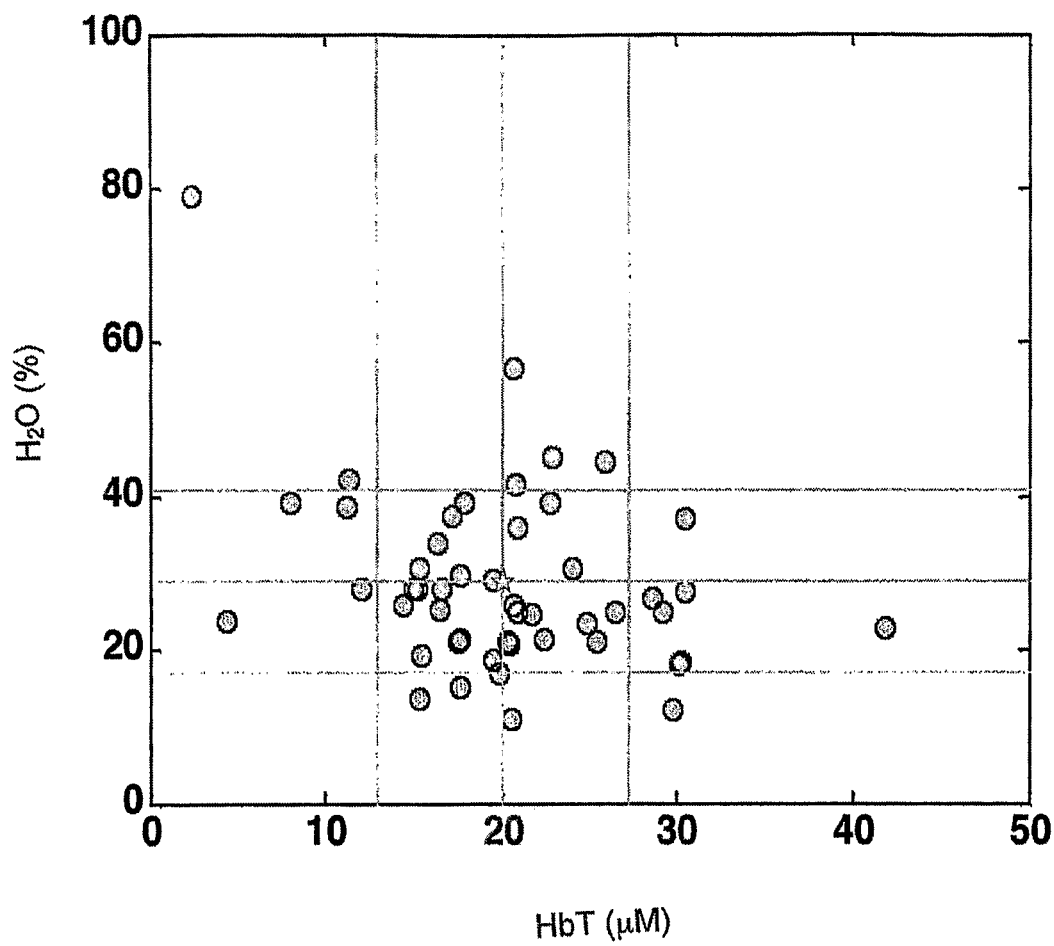
FIG. 12 is a plot showing $H_2O$ versus $HbT$ for the 49 cases.
Figure 13:
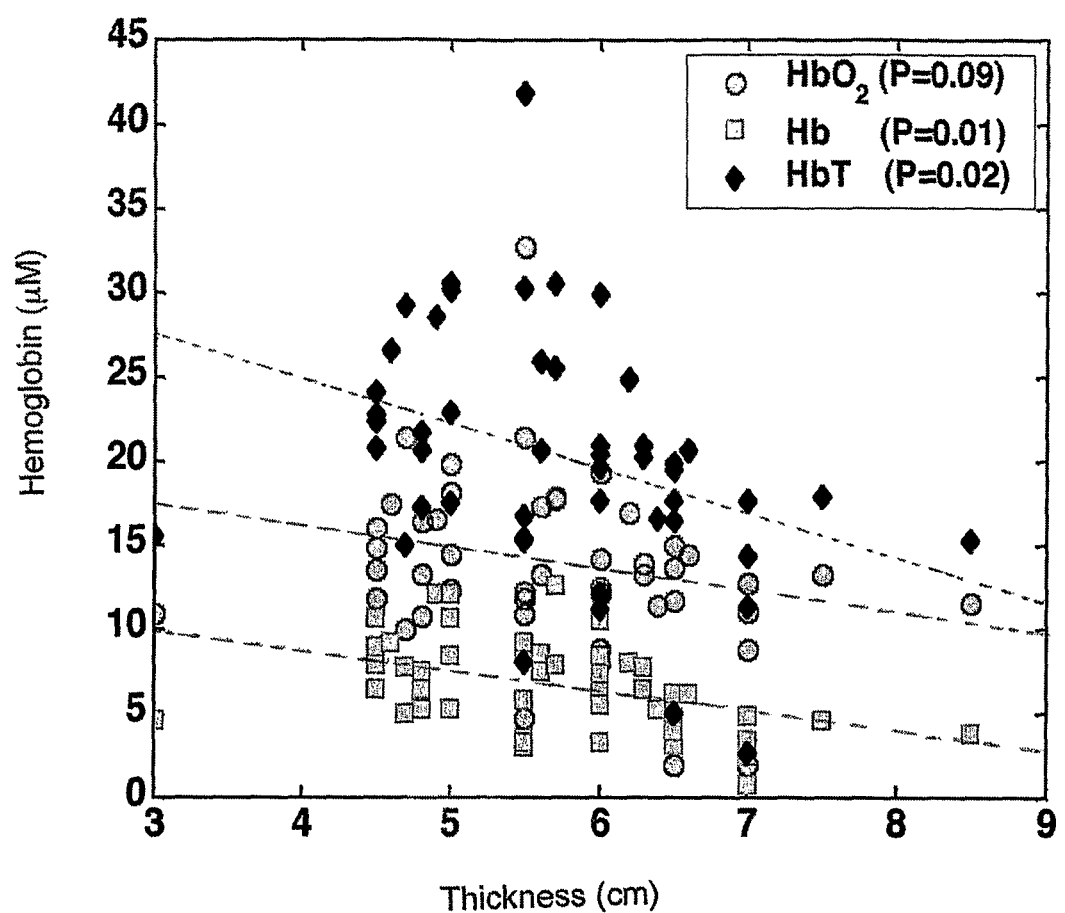
FIG. 13 is a plot of Hb vs thickness (P<0.01)
Figure 14:
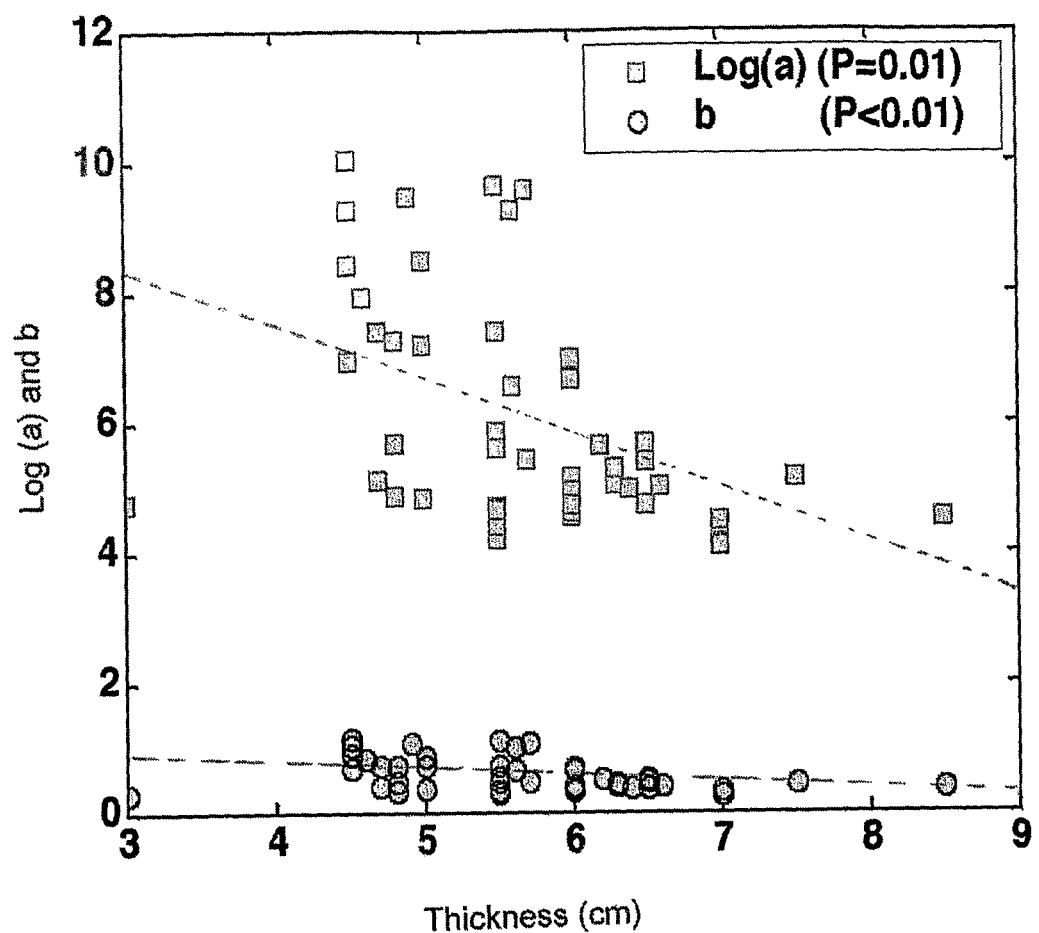
FIG. 14 is a plot of log (a) and b vs thickness (P<0.01; P=0.01)
Figure 15:
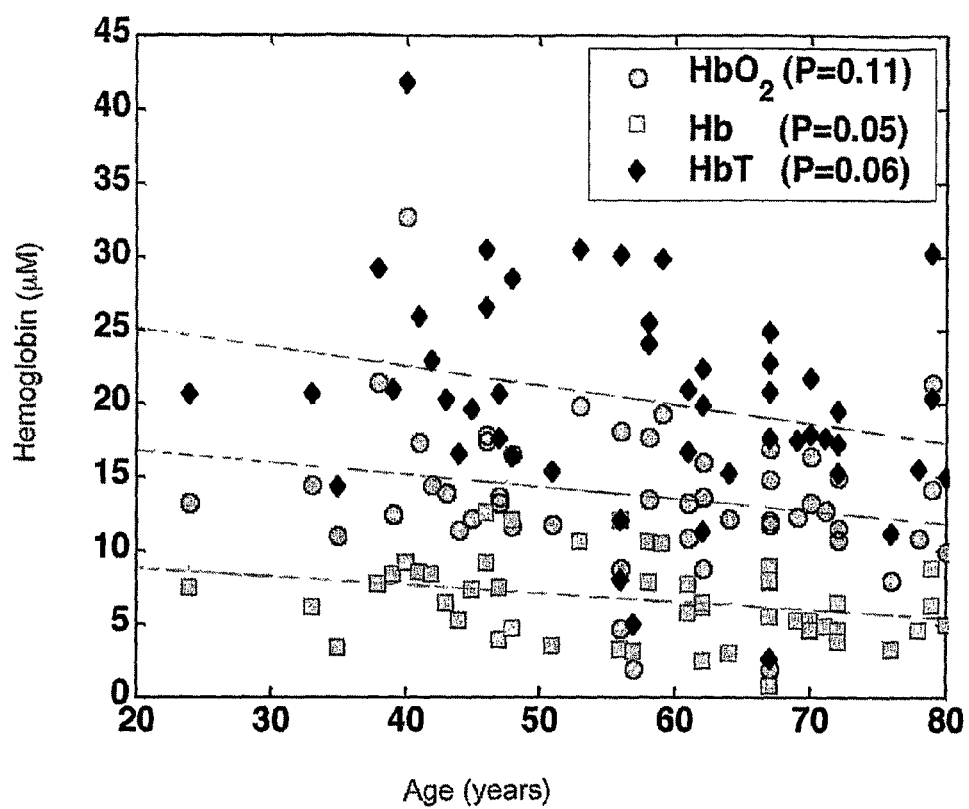
FIG. 15 is a plot of HbO2, Hb and HbT vs age (P=0.10; P=0.05; P=0.06)
Figure 16:
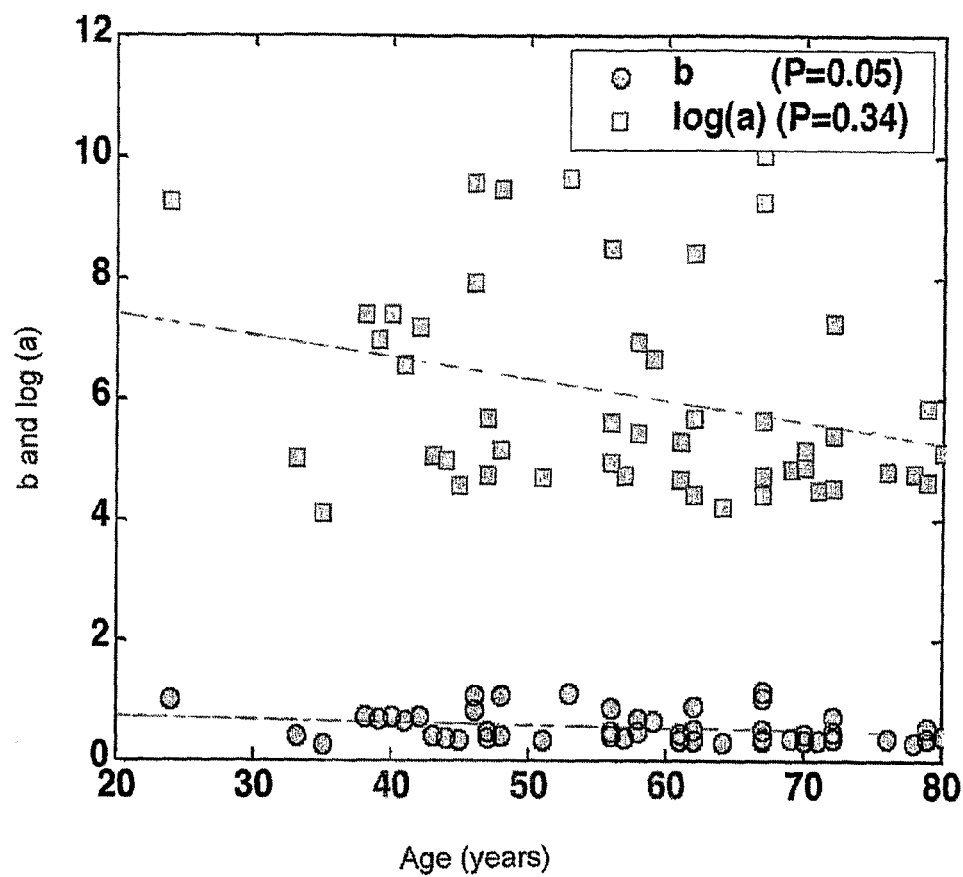
FIG. 16 is a plot of b and log(a) vs age (P=0.05; P=0.34)
Figure 17:
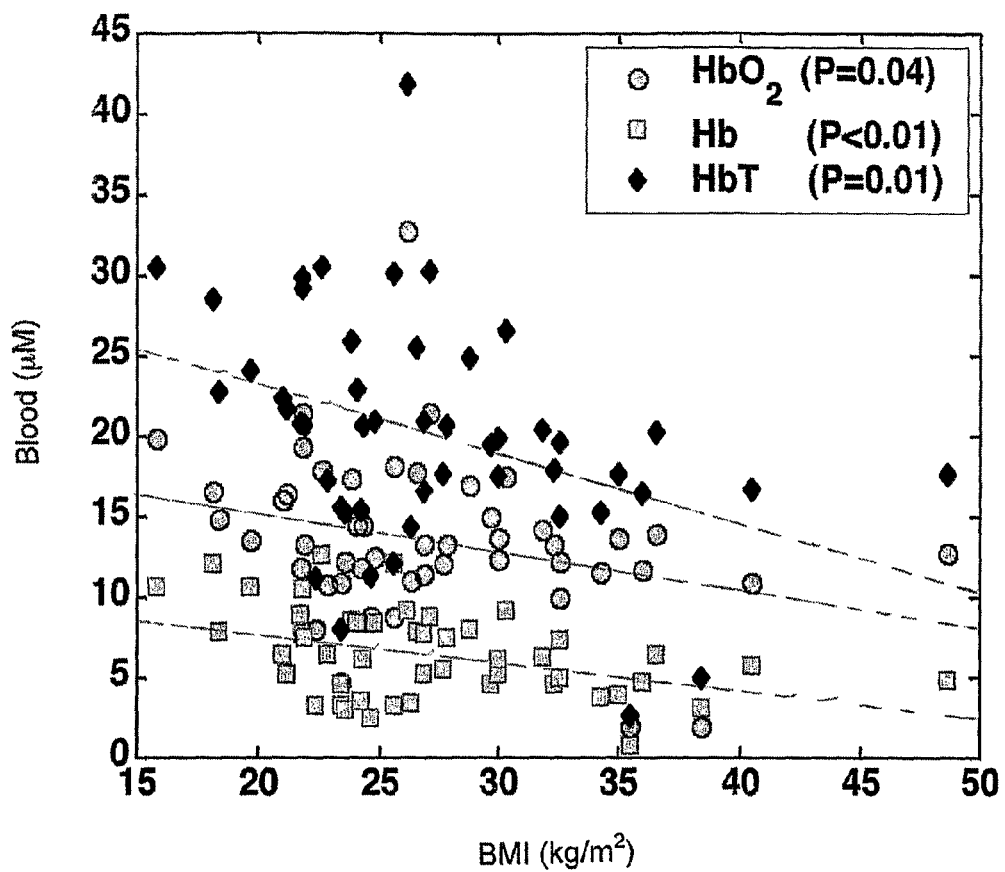
FIG. 17 is a plot of $HbO_2$, Hb and HbT vs BMI (P=0.03; P<0.01; P=0.01)
Figure 18:
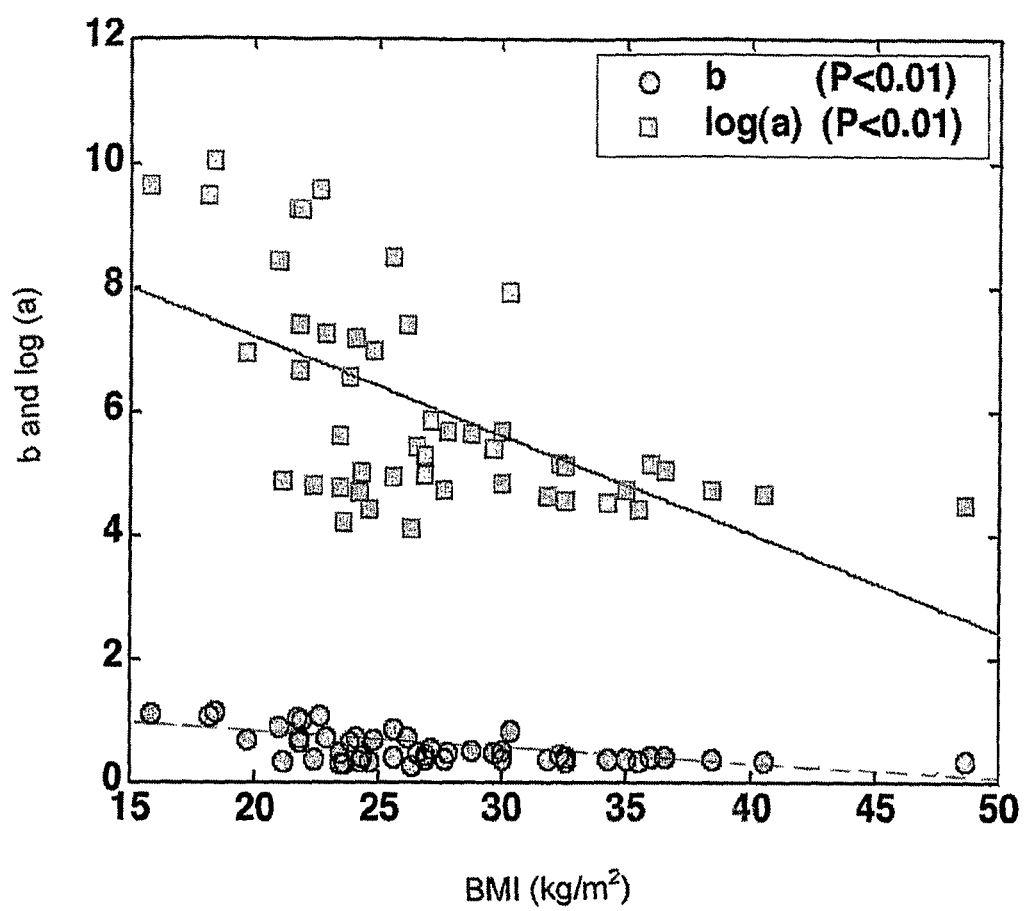
FIG. 18 is a plot of b and log(a) vs BMI (P<0.01; P<0.01)
Figure 19:
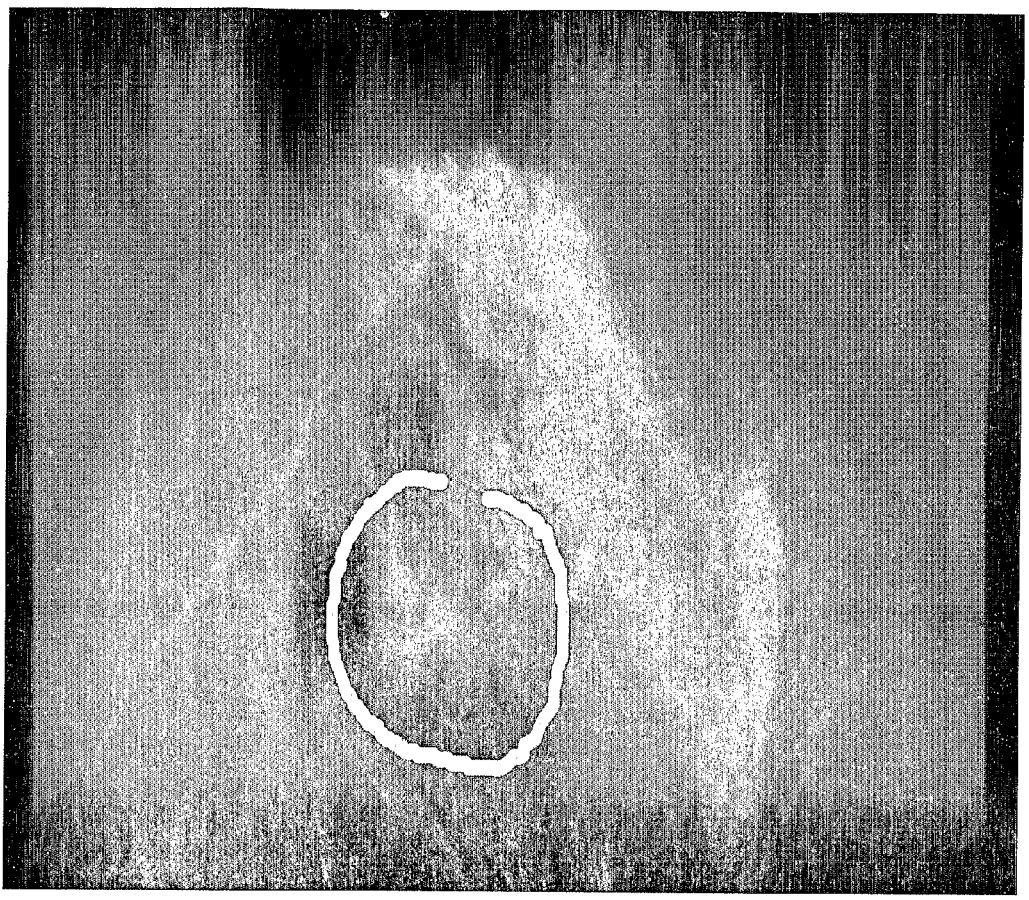
FIG. 19 is an X-Ray craniocaudal view image of the right breast of patient #24 in which a suspicious mass was diagnosed as an infiltrating ductal carcinoma by biopsy.
Figure 20:
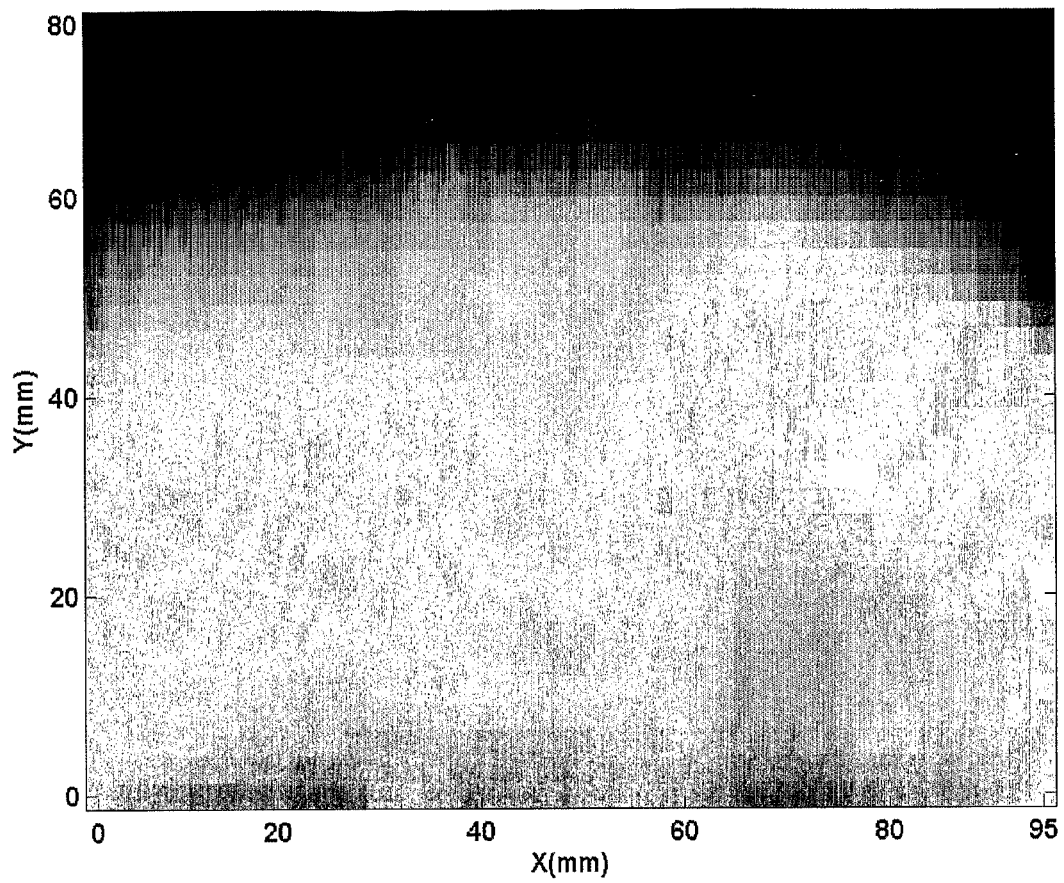
FIG. 20 is a High-resolution optical transmittance image of the breast shown in FIG. 19 (2 mm steps) in the CranioCaudal view.
Figure 21:
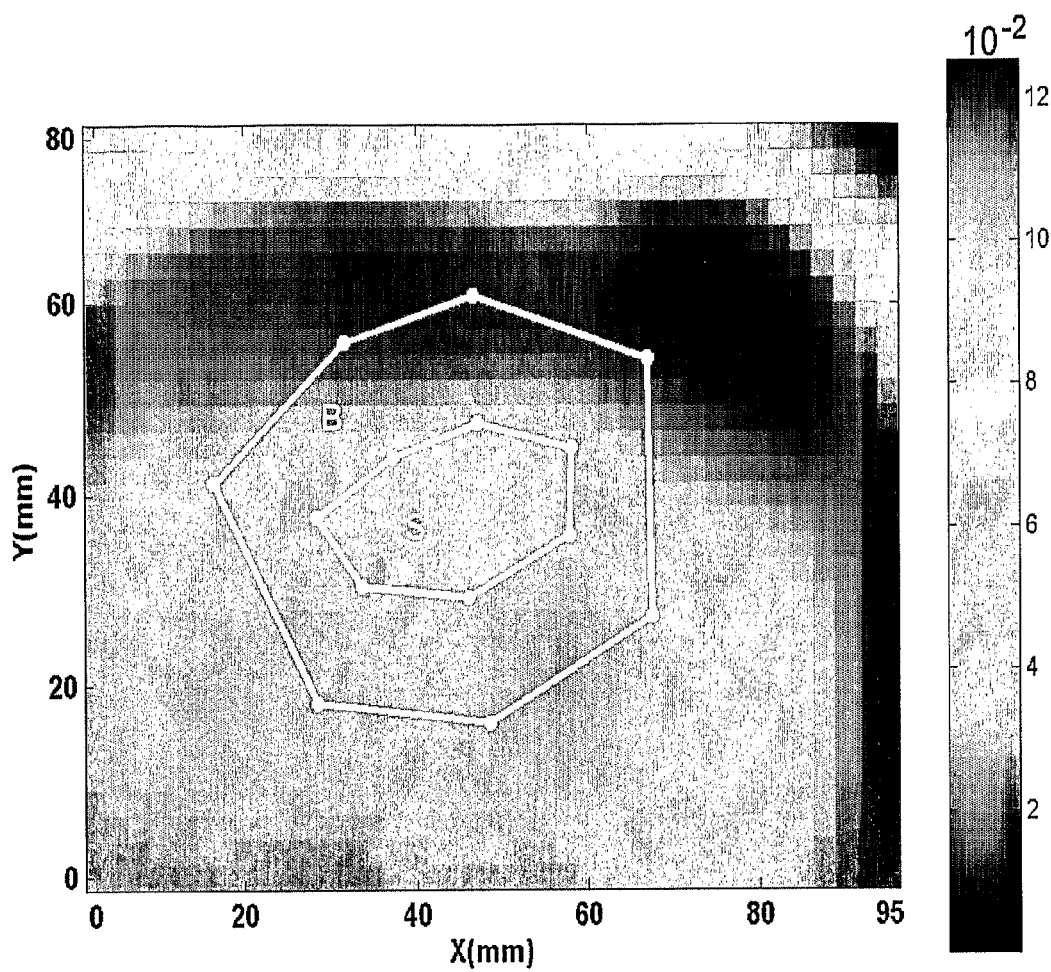
FIG. 21 is a 3D optical reconstruction of the absorption coefficient in which the slice exhibiting the maximum absorption is presented here and in which (S) corresponds to the suspicious ROI and (B) to the background ROI.
Figure 22:
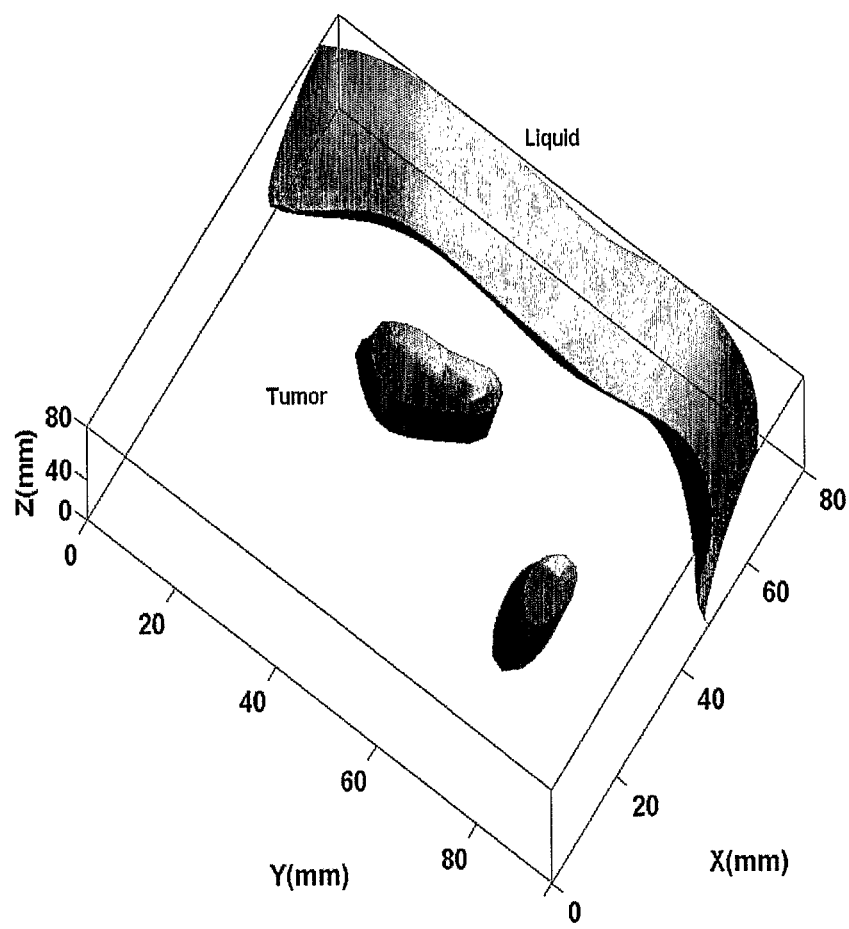
FIG. 22 is a 3D representation using iso-volume of the reconstruction depicted in FIG. 21, the iso-surface was set to 95% of the average $\mu_a$ of the suspected ROI, age=72 years; BMI=34.3 kg/m2; Thickness=8.5 cm.
Figure 23:
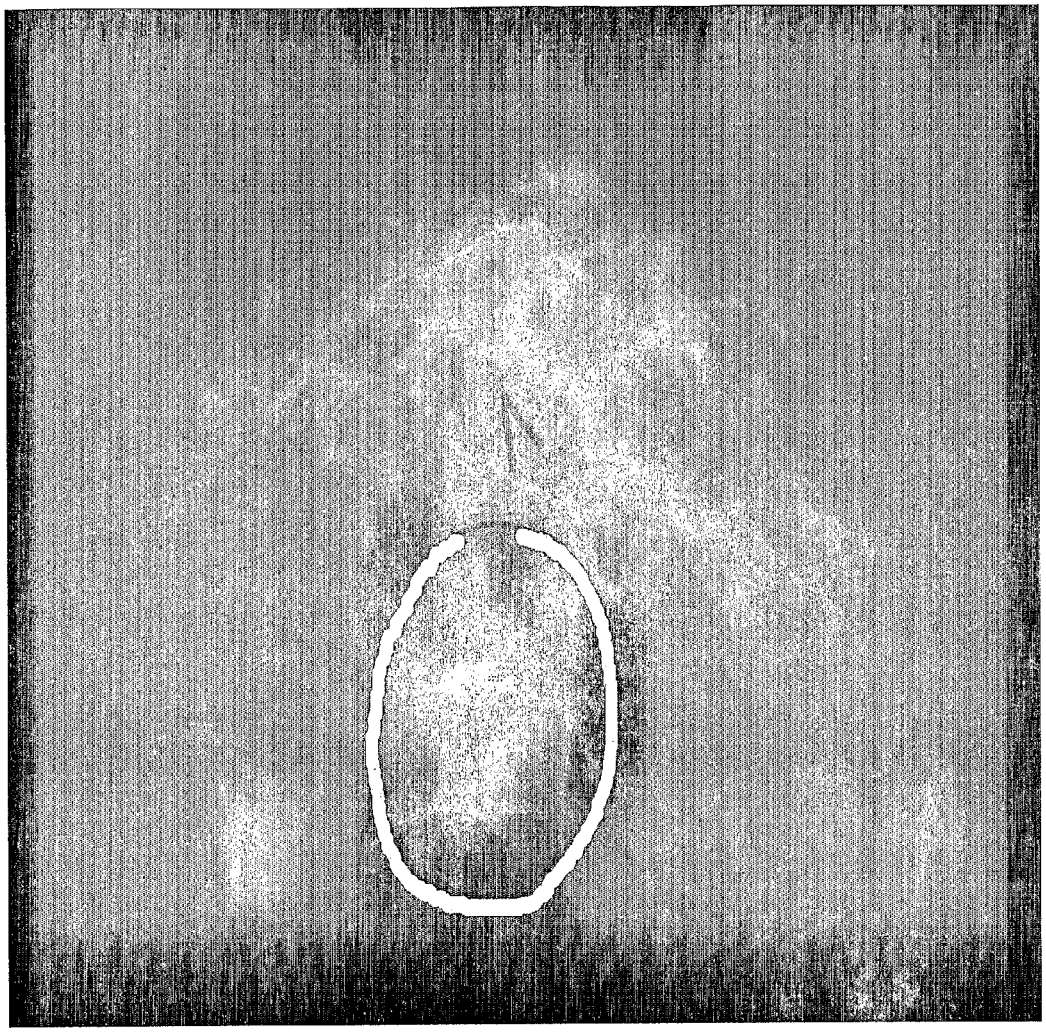
FIG. 23 is an X-Ray CranioCaudal view image of the right breast of patient #59 in which the suspicious mass was diagnosed as an infiltrating carcinoma by biopsy (The position of the tumor was easily estimated from the surface as long as the skin surface was rough like a "peau d'orange" which indicates a malignant obstruction of the superficial lymphatic channels)
Figure 24:
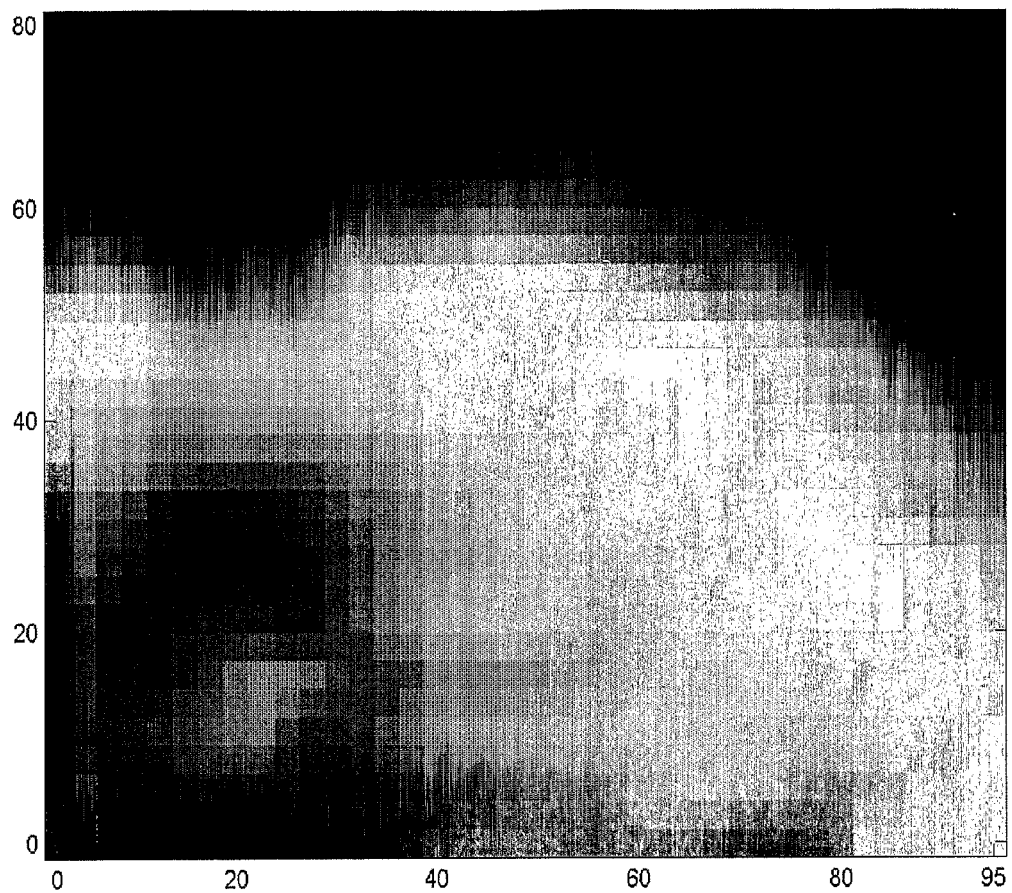
FIG. 24 is a High-resolution optical transmittance image (5 mm steps) in the CranioCaudal view.
Figure 25:
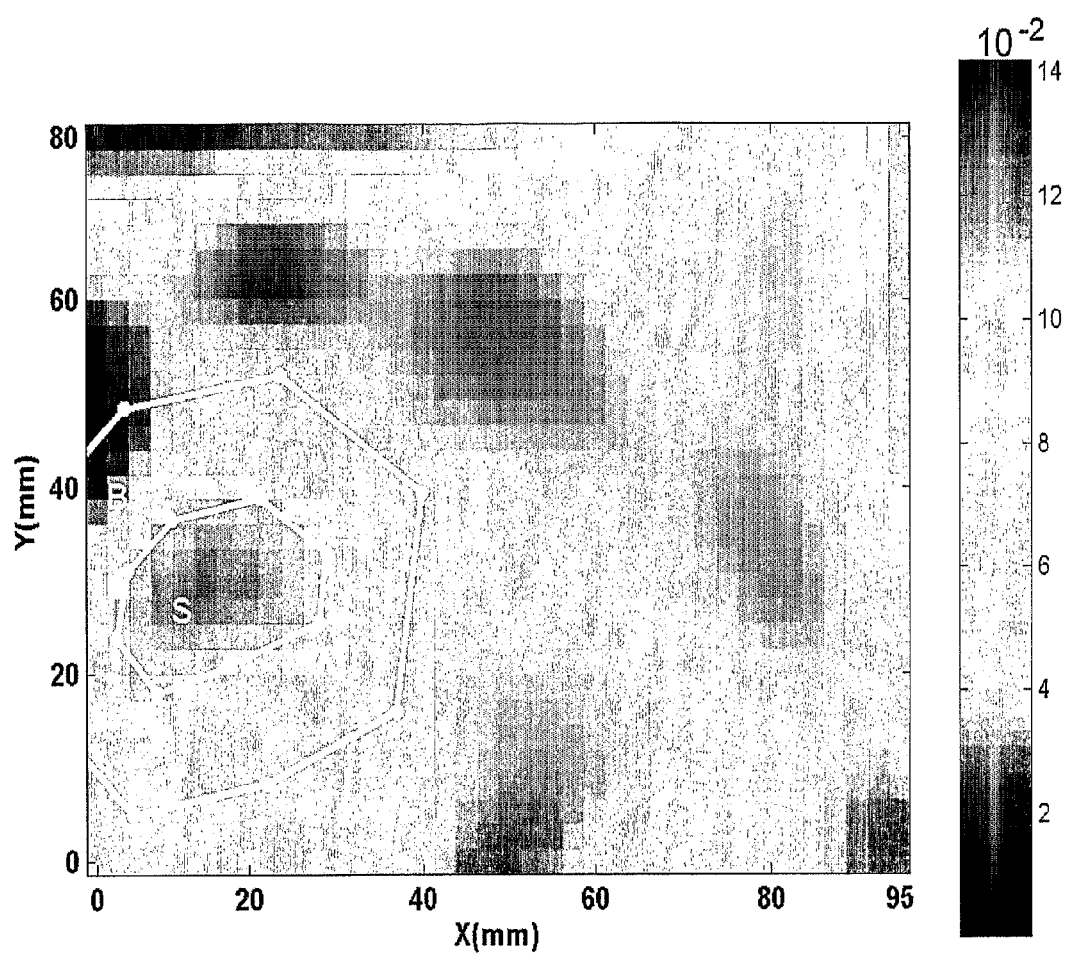
FIG. 25 is a 3D optical reconstruction of the absorption coefficient in which (S) Corresponds to the suspicious ROI and (B) to the background ROI.
Figure 26:
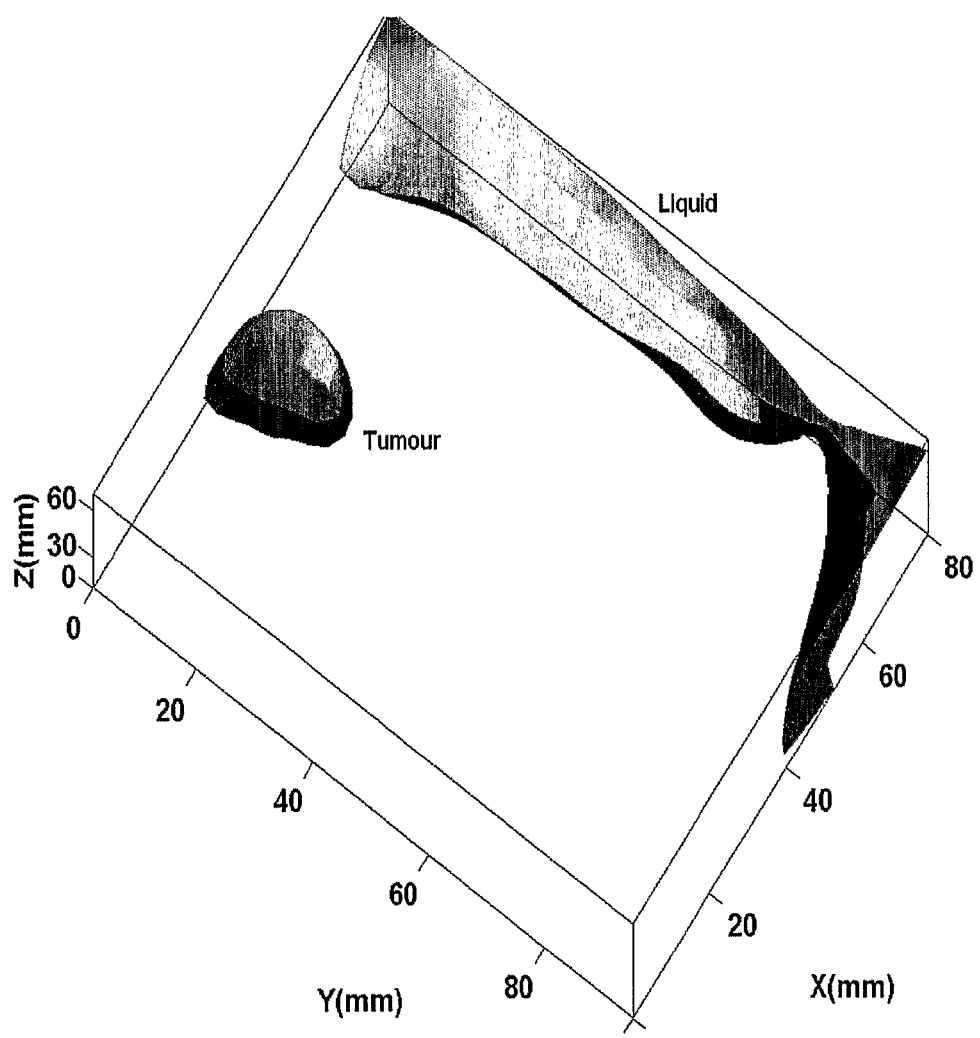
FIG. 26 is a 3D representation using iso-volume of the reconstruction depicted in c), the iso-surface was set to 95% of the average $\mu_a$ of the suspected ROI, age=67 years; BMI=27.7 kg/m2; Thickness=6 cm.
Figure 27:
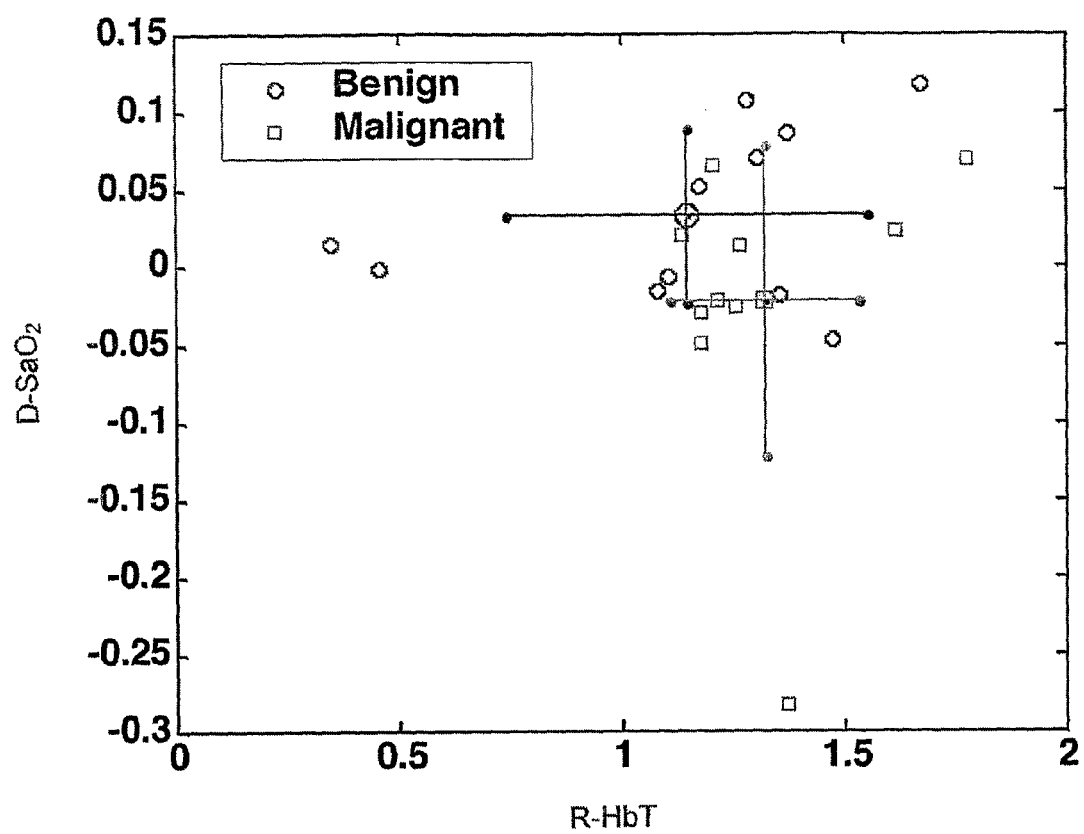
FIG. 27 is a plot of contrast function for R-HbT vs D-SaO$_2$ in which the benign cases are depicted by open circles, and the malignant by red squares and the average values of Table 7 are presented with the filled markers and the associated standard deviation with dashed lines.
Figure 28:
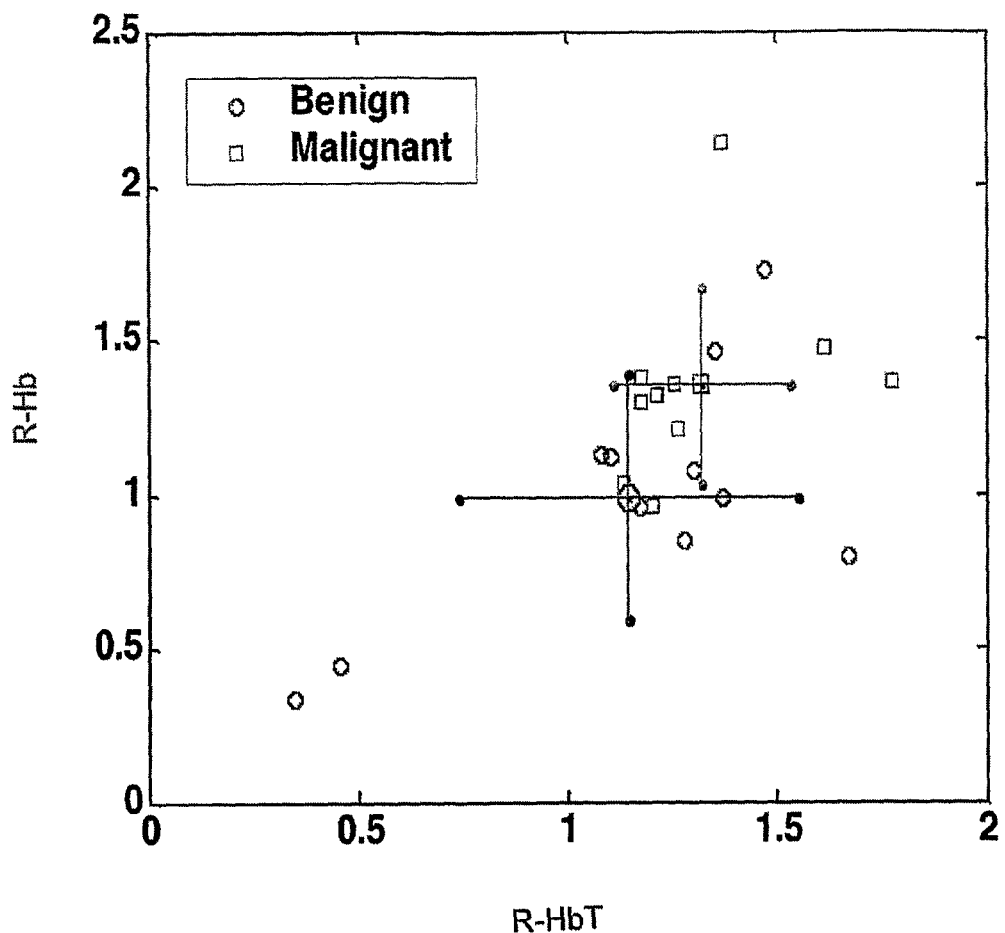
FIG. 28 is a plot of contrast function for R-HbT vs D-Hb in which the benign cases are depicted by open circles, and the malignant by open squares and the average values of Table 7 are presented with the filled markers and the associated standard deviation with dashed lines.
Figure 29:
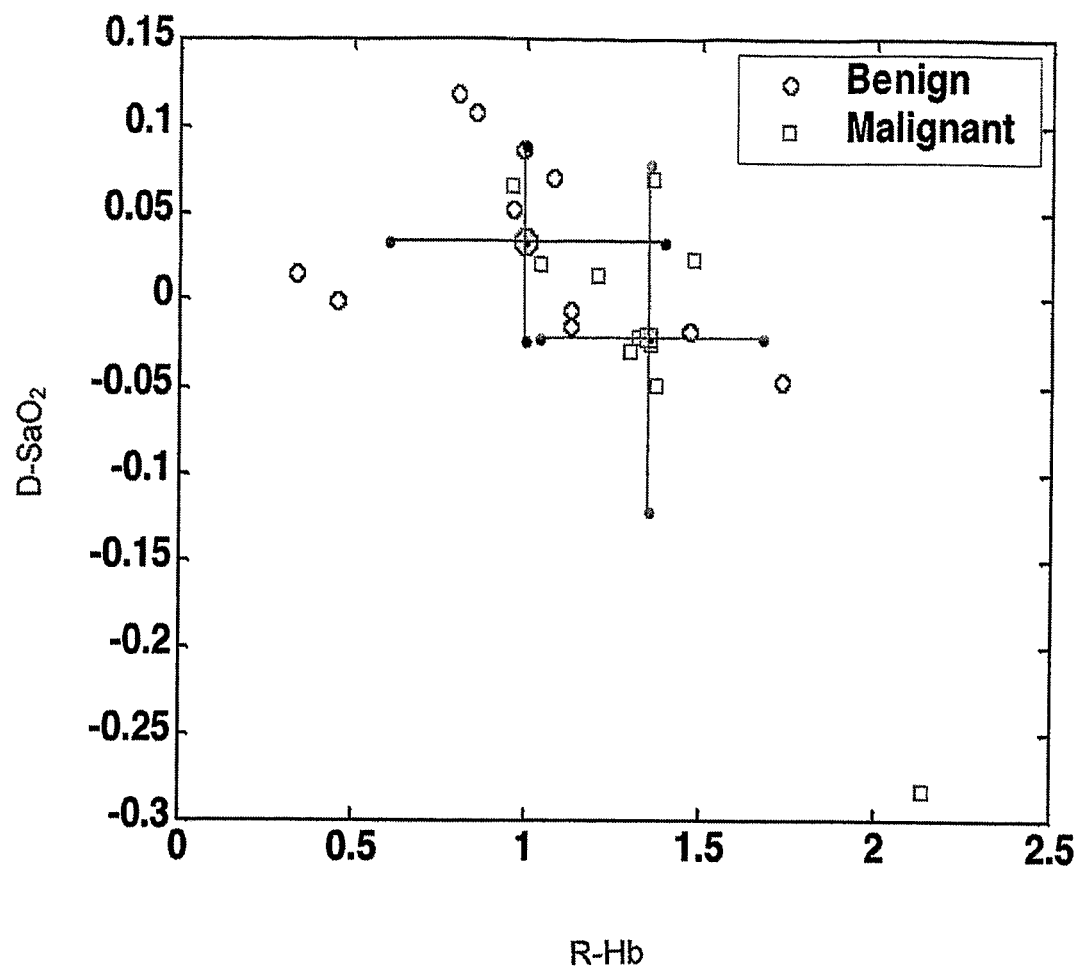
FIG. 29 is a plot of contrast function for R-Hb vs D-SaO$_2$ in which the benign cases are depicted by open circles, and the malignant by open squares and the average values of Table 7 are presented with the filled markers and the associated standard deviation with dashed lines.
Figure 30:
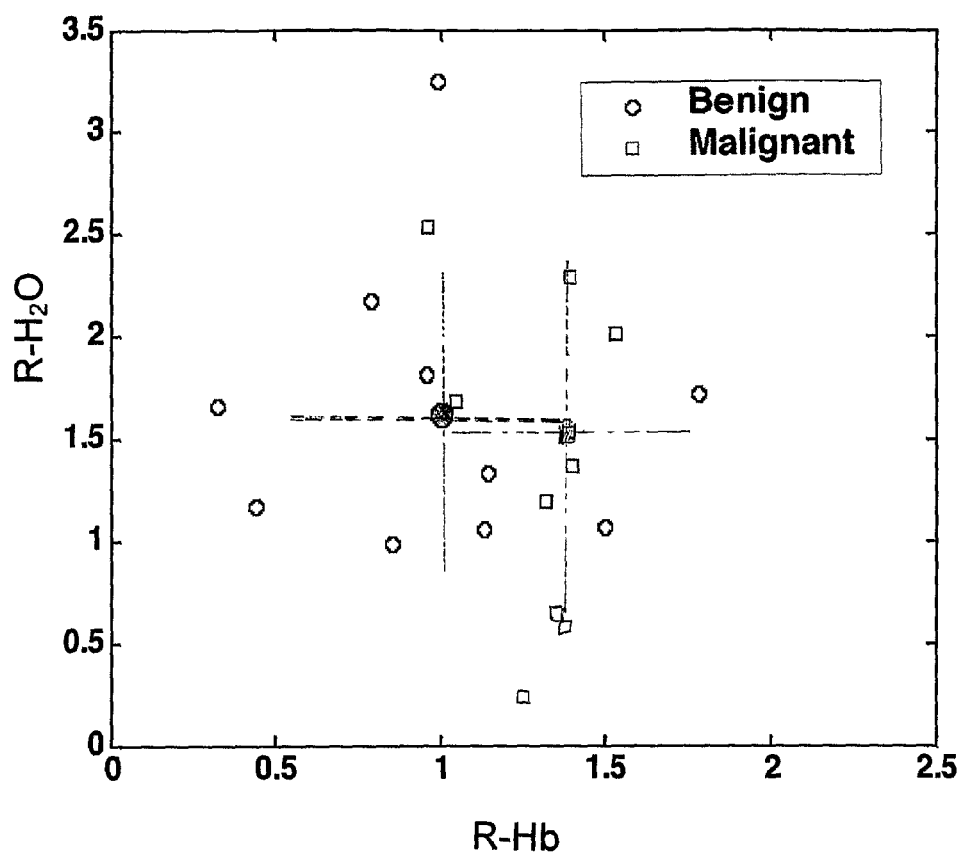
FIG. 30 is a plot of contrast function for R-Hb vs R-H$_2$O in which the benign cases are depicted by open circles, and the malignant by open squares and the average values of Table 7 are presented with the filled markers and the associated standard deviation with dashed lines.

The chromophore concentrations and the scattering power law parameters were estimated following the procedure described above. An example of the fitting results is depicted in FIGS. 7 and 8.

The physiological parameters were estimated patient by patient and the same descriptive statistics were applied to the population. The results are summarized in Table 4.

TABLE 4

Physiological parameters of the recruited population (N = 49).
The statistics are derived from each individual patient.

|  | Minimum | Maximum | Mean | Std Deviation |
|---|---|---|---|---|
| HbT (μM) | 3.0 | 42.1 | 20.4 | 7.1 |
| SaO$_2$ (%) | 51.0 | 89.6 | 71.1 | 7.7 |
| H$_2$O (%) | 11.0 | 76.1 | 28.9 | 11.7 |
| Li (%) | 33.1 | 76.6 | 62.4 | 12.6 |
| Log(a) | 4.1 | 10.3 | 6.0 | 1.7 |
| b | 0.26 | 1.14 | 0.55 | 0.25 |

The chromophores distribution is depicted in FIG. 9 to 12. We do not render the lipid as it is estimated through the scattering coefficients (see equation (6)).

These values are also consistent with the literature (Cerussi et al. Acad Radiol 2001, 8:211; Durduran et al. Phys Med Biol. (2002); 47:2847-2861; Spinelli et al. J. Biomed Opt. 2004, 9:1137; Quarasima et al. Photochem. Photobiol 1998, 67:4; Srinivasan et al. PNAS 2003, 100:12349; Shah et al. J Biomed Opt. 2004, 9:534-540; Progue et al. J Biomed Opt. 2004, 9:541). In the light of references Chernomordik et al., J. Biomed. Opt. 2002; 7:80-87 and Fantini et al., Appl. Opt. 1998; 37:1982-1989, the bounds of the optical and physiological variation within the same breast fall well within the range of the properties of Table 3 and Table 4.

In one embodiment of the invention the potential of the Softscan® platform to successfully acquire useful data over a broad population, especially in regard to the hormonal status of the patient was assessed. The ability of the platform to image breast tissue was demonstrated for the whole population enrolled, even for the dense young breast. Some insight into the correlation between demographic parameters and extracted breast properties is provided here. The investigation preferentially concerned three main parameters described in

TABLE 3

Optical properties encountered during the pre-clinical protocol (N = 49) for the four wavelengths. SD corresponds to the standard deviation. The units are in cm$^{-1}$.

| | 760 nm | | | 780 nm | | | 830 nm | | | 850 nm | | |
|---|---|---|---|---|---|---|---|---|---|---|---|---|
| | Min | Mean ± SD | Max | Min | Mean ± SD | Max | Min | Mean ± SD | Max | Min | Mean ± SD | Max |
| $\mu_a$ | 0.021 | 0.051 ± 0.014 | 0.084 | 0.010 | 0.044 ± 0.014 | 0.081 | 0.014 | 0.051 ± 0.013 | 0.095 | 0.015 | 0.056 ± 0.015 | 0.105 |
| $\mu_s'$ | 7.795 | 10.9 ± 1.1 | 15.5 | 7.7 | 10.7 ± 1.4 | 15.3 | 7.8 | 10.3 ± 1.3 | 15.4 | 7.674 | 10.2 ± 1.6 | 15.3 |

Table 4: age, Body Mass Index (BMI) and thickness (distance between the stabilizing plates).

The summary of the correlation of demographic and physiological properties is provided in Table 5. The correlation coefficient with the 95% confidence interval is given as well as the P values. A value of P<0.05 was considered a significant correlation.

TABLE 5

Correlation of NIR parameters with demographic factors.

| | Factor | Correlartion | 95% confidence Interval | P |
|---|---|---|---|---|
| HbT (µM) | Thickness | −0.34 | −0.57; −0.07 | 0.02 |
| | Age | −0.27 | −0.52; 0.01 | 0.06 |
| | BMI | −0.38 | −0.60; −0.11 | 0.01 |
| $SaO_2$ (%) | Thickness | 0.38 | −0.11; 0.60 | 0.08 |
| | Age | 0.20 | −0.09; 0.45 | 0.18 |
| | BMI | 0.22 | −0.60; 0.07 | 0.13 |
| $H_2O$ (%) | Thickness | −0.02 | −0.30; 0.26 | 0.88 |
| | Age | −0.08 | −0.35; 0.20 | 0.58 |
| | BMI | −0.13 | −0.40; 0.15 | 0.36 |
| a | Thickness | −0.35 | −0.57; −0.07 | 0.01 |
| | Age | 0.14 | −0.40; 0.15 | 0.34 |
| | BMI | −0.49 | −0.68; −0.20 | <0.01 |
| b | Thickness | −0.46 | −0.65; −0.20 | <0.01 |
| | Age | −0.28 | −0.52; 0.00 | 0.05 |
| | BMI | −0.58 | −0.74; −0.35 | <0.01 |

Strong correlations between the demographics parameters and NIR properties are observed. Firstly, the total blood content was significantly correlated to the thickness (P=0.02) and BMI (P=0.01). Generally, a lower thickness and a greater BMI corresponded to a decrease in HbT. These findings are in agreement with ref O'Leary, PhD University of Pennsylvania, 1996 and Grosenick et al., Applied Optics, 2003; 42:3170-3186 (P=0.04 with BMI). A greater BMI is consistent with a greater tissue fat content through a higher ratio of fat to glandular tissue. Higher fat content correlates with lower blood content compared to glandular tissue as demonstrated by compositional analysis data (Duck. Academic Press (1990); 320-328; H Q Woodard et al. Br. J. Radiol. (1986); 59:1209-1219).

Secondly, the saturation was not significantly correlated to any demographic parameter investigated herein. Only an almost significant correlation was noticed with the thickness P=0.08). The same weak or non-existent correlation of the $SaO_2$ has been reported in the above-mentioned references.

Thirdly, the water content, as measured with the current protocol, did not present any correlation with demographic factors. Srinivisan et al. PNAS, 2003; 100:12349-12354, reported a weak correlation between water and age (P=0.06) and Cerussi et al. found correlation between water, lipid and age.

Finally, the parameters of the scatter power law exhibited strong correlation with demographic factors (P<0.01). Both parameters were significantly correlated to the BMI. As stated above, these two parameters are related to the physiology of the breast and are sensitive to the scattering center size and density. The BMI reflects indirectly the structural composition of the breast. Moreover, a highly significant correlation (P<0.01 assessed by one-way ANOVA) between the radiographic density and BMI was found, highlighting the relationship between and structural composition of the breast. Similarly, the scattering amplitude and scattering power are significantly correlated to the thickness (P=0.01 and P<0.01 respectively). In this case also, we found a highly significant correlation between the BMI and the thickness (P<0.01). Generally the higher thickness were associated with large breasts exhibiting smaller amount of fibro glandular tissues. The scattering power was significantly correlated to age (P=0.05). The same correlation was noticed in reference T Durduran et al. Phys Med Biol. (2002); 47:2847-2861 and B Tromberg et al. Neoplasia (2000); 2:26-40 (P=0.05).

The different NIR parameters that presented correlation with some demographic factors are displayed in FIG. 13 to 18.

Overall, the correlation of the breast NIR properties with demographics factors was in agreement with expected physiology of the breast and with previously published work. These findings confirm the potential of optical spectroscopy to reveal physiologically relevant information about biological tissues.

Detection and Characterization of Breast Tumors

Among the 49 patients selected in the previous section, 47 had suspicious masses. However, due to the limited size of the ROI captured in the present example, only in 23 cases was the suspicious mass within the optical ROI. Eleven (11) of these cases were confirmed as malignant and twelve (12) as benign by biopsy. For all 23 cases, a suspicious ROI was defined (referred as (S)). This suspicious ROI was defined through consensus conference of an in-house group comprised of scientists and clinical personnel. Examples of clinical cases data are provided in FIG. 19 to FIG. 26.

An annulus encompassing the suspicious ROI was defined automatically with the same number of voxels as (S) and was used to define a healthy background surrounding tissue ROI (B). Both ROIs were selected in the reconstruction slice (slice parallel to the stabilizing plates) exhibiting the maximum absorption contrast in the suspicious ROI. The average optical absorption for both ROI was computed at each wavelength. Then, the local physiological parameters of both ROIs were derived using the NNLS algorithm for the lipid-corrected absorption. The estimated physiological values for all the suspicious areas of the breast masses imaged are shown in Table 6. It will be appreciated that while in the above example the background is obtained from an area immediately surrounding the suspicious area, it can also be obtained for other regions in the tissue. An average of the optical property and/or physiological characteristics of several non-suspicious regions may also be obtained and compared to the suspicious region.

Table 6 represents absolute values of the chromophore concentrations. In both the cases of malignant and benign pathologies, the masses exhibited on average a significantly higher blood volume. Only in two benign cases (patient #21: Juvenile fibro-adenoma and patient #22 cyst diagnosed by ultrasound), was the total blood volume of the suspicious mass found to be inferior to the background value, which was to be expected in the case of patient #22 considered to the pathology of the suspicious masses (X Gu et al. Acad. Radiol. (2004); 11:53-60). Besides these two cases, the suspicious masses were clearly discriminated from the background. This increase in total hemoglobin is expected as it reflects an increased vascularization (A E Profio et al. Med. Phys. (1989); 16:60-65; G W Sledge Jr et al. Eur J Cancer (2003); 39:1668-1675). Such optically derived contrast in blood volume is consistent with results obtained by several authors (H Dehghani et al. Applied Optics (2003); 42:135-45; B Tromberg et al. Neoplasia (2000); 2:26-40; V Chernomordik et al. J. Biomed. Opt. (2002); 7:80-87; S Fantini et al. Appl. Opt. (1998); 37:1982-1989). Especially, Grosenick et al. found the same consistent total blood volume increase between healthy and tumoral tissue from 50 patients (D Grosenick et al. Phys Med. Biol. (2004); 49:1165-1181). However, from the absolute values of the total blood volume, there is no obvious discrimination between the benign and malignant pathologies. The average total blood volume was similar in both cases.

TABLE 6

Optically derived physiological parameters for the breast masses imaged. The mean, standard deviation and [minimum; maximum] are provided for the suspicious ROI (S) and the background ROI (B).

|  |  | HbT (µM) | SaO$_2$ (%) | H$_2$O (%) |
|---|---|---|---|---|
| Malignant | (S) | 27.7 ± 9.2 [14.8; 48.8] | 67.9 ± 16.2 [20.9; 78.7] | 40.8 ± 16.6 [10.4; 64.0] |
|  | (B) | 20.3 ± 4.2 [13.0; 27.5] | 70.3 ± 8.2 [49.3; 82.6] | 38.2 ± 21.7 [23.3; 96.4] |
| Benign | (S) | 27.1 ± 10.9 [8.4; 44.4] | 70.6 ± 10.6 [50.5; 89.3] | 49.5 ± 20.0 [23.6; 90.2] |
|  | (B) | 23.8 ± 4.2 [16.0; 28.7] | 67.3 ± 9.6 [49.1; 78.7] | 42.9 ± 19.8 [12.5; 77.5] |

The saturation did not provide a clear discrimination between background and suspicious ROI. The differences observed between the two ROIs fell within the uncertainty defined by the standard deviation. In the case of saturation, this behavior has been reported also in previous work (H Dehghani et al. Applied Optics (2003); 42:135-45; B Tromberg et al. Neoplasia (2000); 2:26-40; V Chernomordik et al. J. Biomed. Opt. (2002); 7:80-87; S Fantini et al. Appl. Opt. (1998); 37:1982-1989; D Grosenick et al. Phys Med. Biol. (2004); 49:1165-1181; D Jakubowski et al. J. Biomed. Opt. (2004); 9:230-238. Both increased and decreased oxygen in the suspicious mass compared to the background was encountered.

Lastly, the water concentration was on average greater in the suspicious mass compared to the background ROI. This was true both for the malignant and the benign masses. This finding is also consistent with previously published work (D Jakubowski et al. J. Biomed. Opt. (2004); 9:230-238.

Due to the distribution of the physiological parameters among the population for the healthy tissue, the contrast between the suspicious and the background ROIs was also investigated. The contrast was defined as the individual ratio of the mean values of the HbO$_2$, Hb, HbT and H$_2$O concentrations and the difference in SaO$_2$ values between the two ROIs. The summary of these contrasts is provided in Table 7.

TABLE 7

Contrast between the suspicious ROI average physiological parameters and the healthy surroundings. The contrast for the saturation was defined as a difference (D-) whereas it was defined as a ratio for all other parameters (R-).

|  | R-HbO$_2$ | R-Hb | R-HbT | D-SaO$_2$ | R-H$_2$O |
|---|---|---|---|---|---|
| All cases | 1.22 ± 0.41 | 1.17 ± 0.41 | 1.22 ± 0.34 | 3.74 ± 8.38 | 1.48 ± 0.62 |
| Malignant | 1.28 ± 0.35 | 1.41 ± 0.36 | 1.34 ± 0.25 | −2.40 ± 9.55 | 1.47 ± 0.76 |
| Benign | 1.19 ± 0.48 | 0.98 ± 0.42 | 1.13 ± 0.42 | 2.92 ± 5.76 | 1.50 ± 0.47 |

The values in Table 7 underline the findings of Table 6. An increase in HbO$_2$, Hb and hence HbT occurs consistently for the imaged masses. Also, an increase in water content is clearly seen with however more dispersion. In this particular example, the saturation seems not to provide a consistent trend.

When the population is separated between the malignant and benign pathologies, interesting differences appear. First, malignant lesions have a greater total hemoglobin concentration surrounding tissue than benign lesions. The contrast is more marked when only the contribution of deoxy-hemoglobin is considered. Then the discrimination between malignant and benign lesions, on average, is more pronounced. The malignant masses clearly exhibit a higher Hb content compared to surrounding tissue than benign cases. These findings are consistent with the expectation that malignant tumors are more metabolically active than benign lesions. Using the protocol of the present example there was no other clear discrimination when investigating the other contrast functions. FIG. 27 to 30 show plots of the contrast function exhibiting the most important discrimination between malignant and benign pathologies.

While the example provided above pertains to breast tissue, any other tissue amenable to optical data acquisition is encompassed within the scope of the invention.

The embodiment(s) of the invention described above is(are) intended to be exemplary only. The scope of the invention is therefore intended to be limited solely by the scope of the appended claims.

We claim:

1. A method for detecting an abnormality within a tissue said method comprising using a processing unit:
   obtaining measurements of said tissue using a plurality of optical source-detector pairs;
   applying a non-linear least square (NNLS) solution of an inverse problem to said measurements to determine optical properties of constituents of said tissue;
   optically reconstructing a volume of said tissue by synthesizing said measurements through the NNLS solution of the inverse problem; the NNLS solution being derived from the equation:

$$\mu_a(\lambda) = \sum_i^{NC} \varepsilon_i^\lambda C_i$$

where $$\varepsilon_i^\lambda$$

is the wavelength dependent extinction coefficient of the i-th chromophore and $C_i$ its concentration;

obtaining a value related to an optical property of said tissue from each of at least two regions of interest (ROIs), wherein said at least two ROIs are contained within said optically reconstructed volume of said tissue;

comparing pair-wise said values from said at least two ROIs to generate, for each ROI pair of the at least two ROIs, a ratio of said values, wherein said ratio is indicative of a presence of said abnormality in one of said at least two ROIs.

2. The method as claimed in claim 1 wherein said optical property is selected from absorption, scatter coefficient and combination thereof.

3. The method as claimed in claim 1 wherein said optical property is correlated with a physiological property value.

4. The method as claimed in claim 3 wherein said physiological property value is selected from oxy-hemoglobin concentration, deoxy-hemoglobin concentration, total hemoglobin concentration, water content, lipid concentration, oxygen saturation, scattering power (b), scattering amplitude (b) and combination thereof.

5. The method as claimed in claim 1 wherein said at least two ROIs are selected by inspection of an optical image of said tissue and wherein one of said at least two ROIs exhibits optical properties different from its surroundings.

6. The method as claimed in claim 1 wherein said abnormality is correlated with a disease state.

7. The method as claimed in claim 6 wherein said ratio is concentration of hemoglobin in said abnormal region and in another region.

8. The method as claimed in claim 6 wherein said disease state is a cancer.

9. The method as claimed in claim 8 wherein said tissue is breast tissue and said cancer is breast cancer.

10. A method for characterizing an abnormality in a tissue, said method comprising using a processing unit:

analyzing said tissue with one or more modalities other than optical imaging;

identifying, based on said one or more modalities, an abnormal region of the tissue;

identifying, based on said one or more modalities, a normal region;

obtaining measurements of said tissue using a plurality of optical source-detector pairs;

applying a non-linear least square (NNLS) solution of an inverse problem to said measurements to determine optical properties of constituents of said tissue;

optically reconstructing a volume of said tissue by synthesizing said measurements through the NNLS solution of the inverse problem, wherein said normal region and said abnormal region are contained within said optically reconstructed volume of said tissue; the NNLS solution being derived from the equation:

$$\mu_a(\lambda) = \sum_i^{NC} \varepsilon_i^\lambda C_i$$

where $$\varepsilon_i^\lambda$$

is the wavelength dependent extinction coefficient of the i-th chromophore and $C_i$ its concentration;

obtaining a first value related to an optical property of said abnormal region;

obtaining a second value related to said optical property of said normal region;

deriving a first physiological property value from said optical property of said abnormal region;

deriving a second physiological property value from said optical property of said normal region; and characterizing said abnormal region based on a ratio of said first and second derived physiological property values.

11. The method as claimed in claim 10 wherein said abnormal regions identified based on said one or more modalities are registered with corresponding ROIs in an optical image of said tissue.

12. The method as claimed in claim 10 wherein said optical property is selected from absorption, scatter coefficient and combination thereof.

13. The method as claimed in claim 10 wherein said physiological property is selected from oxy-hemoglobin concentration, deoxy-hemoglobin concentration, total hemoglobin concentration, water content, lipid concentration, oxygen saturation, scattering power (b), scattering amplitude (a) and combination thereof.

14. The method as claimed in claim 10 wherein said normal region is a region surrounding said abnormal region.

15. The method as claimed in claim 10 wherein said one or more modalities are selected from imaging modality, physical examination modalities and combinations thereof.

16. The method as claimed in claim 15 wherein said imaging modality is selected from X-ray imaging, MRI, PET, ultrasound and combination thereof.

17. The method as claimed in claim 10 wherein said step of characterizing further comprises correlating said first physiological property value or said ratio of physiological property values with a disease state.

18. The method as claimed in claim 10 wherein said ratio is a ratio of hemoglobin concentration.

19. The method as claimed in claim 18 wherein said disease state is a cancer.

20. The method as claimed in 19 wherein said tissue is breast tissue and said cancer is breast cancer.

21. A method for establishing a diagnosis of an abnormality within a tissue said method comprising using a processing unit:

obtaining a first diagnosis of said abnormality with a modality other than optical imaging;

determining, based on said first diagnosis, one or more features of said abnormality to be characterized by optical imaging of said abnormality;

obtaining measurements of said tissue using a plurality of optical source-detector pairs;

applying a non-linear least square (NNLS) solution of an inverse problem to said measurements to determine optical properties of constituents of said tissue;

optically reconstructing a volume of said tissue by synthesizing said measurements through the NNLS solution of the inverse problem, wherein a normal region and a region having said abnormality are contained within said optically reconstructed volume of said tissue; the NNLS solution being derived from the equation:

$$\mu_a(\lambda) = \sum_i^{NC} \varepsilon_i^\lambda C_i$$

where $\varepsilon_i^\lambda$ is the wavelength dependent extinction coefficient of the i-th chromophore and $C_i$ its concentration;
- obtaining an optical image of said optically reconstructed volume of said tissue;
- identifying said abnormality within said optical image;
- identifying said normal region in said optical image;
- obtaining a value related to an optical property of said normal region;
- deriving a physiological property value from said optical property of said normal region;
- measuring a physiological property value of said abnormality; and
- characterizing said one or more features by obtaining a ratio of the physiological property values of said normal region and of said abnormality;
- wherein said characterization is indicative of disease state of said tissue.

22. The method as claimed in claim 21 wherein said optical property is selected from absorption, scatter coefficient and combination thereof.

23. The method as claimed in claim 21 wherein said physiological property is selected from oxy-hemoglobin concentration, deoxy-hemoglobin concentration, total hemoglobin concentration, water content, lipid concentration, oxygen saturation, scattering power (b), scattering amplitude and combination thereof.

24. The method as claimed in claim 21 wherein said normal region is a region surrounding said abnormality.

25. The method as claimed in claim 21 wherein said modality other than optical imaging is selected from imaging modality, physical examination modalities and combinations thereof.

26. The method as claimed in claim 25 wherein said imaging modality is selected from X-ray imaging, MRI, PET, ultrasound and combination thereof.

27. The method as claimed in claim 21 wherein said step of characterizing further comprises correlating said physiological property value of said abnormality or said ratio of physiological values with a disease state.

28. The method as claimed in claim 21 wherein said ratio is a ratio of hemoglobin concentration.

29. The method as claimed in claim 28 wherein said disease state is a cancer.

30. The method as claimed in 29 wherein said tissue is breast tissue and said cancer is breast cancer.

* * * * *